United States Patent [19]

Hsiao et al.

[11] Patent Number: 5,275,945
[45] Date of Patent: Jan. 4, 1994

[54] ALKALINE PROTEASES STABLE IN HEAVY-DUTY DETERGENT LIQUIDS

[75] Inventors: Humg-Yu Hsiao; Douglas W. Fodge, both of Rockville, Md.; James J. LaLonde, Round Rock, Tex.

[73] Assignee: Vista Chemical Company, Austin, Tex.

[21] Appl. No.: 772,087

[22] Filed: Oct. 8, 1991

[51] Int. Cl.$^5$ .................. C12N 15/00; C12N 9/52; C12N 9/56; C12N 1/20
[52] U.S. Cl. .................. 435/221; 536/23.2; 435/220; 435/222; 435/252.3
[58] Field of Search .............. 536/23.2; 4335/221, 4335/252.3, 220, 222

[56] References Cited

U.S. PATENT DOCUMENTS

| | | | |
|---|---|---|---|
| 3,674,643 | 7/1972 | Aunstrup et al. | 195/62 |
| 3,827,938 | 8/1974 | Aunstrup et al. | |
| 3,838,009 | 9/1974 | Fukumoto et al. | |
| 3,960,665 | 6/1976 | Villadsen et al. | 195/66 |
| 4,052,262 | 10/1977 | Horikoshi et al. | 195/66 |
| 4,318,818 | 3/1982 | Letton et al. | 252/174 |
| 4,537,706 | 8/1985 | Severson | 252/545 |
| 4,764,470 | 8/1988 | Durham et al. | 435/221 |
| 4,771,003 | 9/1988 | Stellwag et al. | 435/221 |
| 4,797,362 | 1/1989 | Takeuchi et al. | 435/221 |
| 4,900,475 | 2/1990 | Ramachandran et al. | 252/532 |

FOREIGN PATENT DOCUMENTS

| | | |
|---|---|---|
| 214435 | 3/1987 | European Pat. Off. |
| 220921 | 5/1987 | European Pat. Off. |
| 0319460 | 6/1989 | European Pat. Off. |
| 495401 | 7/1992 | European Pat. Off. |
| 496361 | 7/1992 | European Pat. Off. |
| 004236 | 1/1981 | Japan |
| 13490 | 8/1983 | Japan |
| 1243784 | 8/1981 | United Kingdom |
| 2126242A | 3/1984 | United Kingdom |
| 89/06279 | 7/1989 | World Int. Prop. O. |
| 91/00345 | 1/1991 | World Int. Prop. O. |

OTHER PUBLICATIONS

Koki Horikoshi, "Production of Alkaline Enzymes by Alkalophilic Microorganisms, Part I. Alkaline Protease Produced by Bacilius No. 221," Agr. Biol. Chem., vol. 35, No. 9, pp. 1407–1414 (1971).

David A. Estell, et al., "Engineering an Enzyme by Site-directed Mutagenesis to be Resistant to Chemical Oxidation," The Journal of Biological Chemistry, vol. 260, No. 11, pp. 6518–6521 (1985).

Ryuta Kaneko, et al., "Molecular Cloning of the Structural Gene for Alkaline Elastase YaB, a New Subtilisin Produced by an Alkalophilic Bacillus Strain," Jrnl. of Bacteriology, pp. 5232–5236 (1989).

Yukio Takii, et al. "Alkaline Serine Protease Produced from Citric Acid by *Bacillus Alcalophilus* subsp. halodurans KP 1239," Appl. Microbiol. Biotechnology, vol. 34, pp. 57–62 (1990).

Robert J. Delange, et al. "Amino Acid Composition: Isolation and Composition of Peptides From The Tryptic Hydrolysate," The Journal of Biological Chemistry, vol. 245, No. 9, pp. 2134–2141 (1967).

Daisuke Tsuru, et al. "Some Physicochemical Properties and Amino Acid Composition of Alkaline Protease of *Bacillus Subtilis* ", Agr. Biol. Chem., vol. 31, No. 3, pp. 330–335 (1967).

(List continued on next page.)

Primary Examiner—Robert A. Wax
Assistant Examiner—Keith D. Hendricks
Attorney, Agent, or Firm—Foley & Lardner

[57] ABSTRACT

Alkaline proteases that are stable in the presence of linear alkylbenzene sulfonates can be obtained from bacteria isolated from soil and by other means. The soils are collected from an alkaline environment which has been exposed to extremely high pH and/or detergent contamination. The proteases are at least twice as stable as Esperase TM when stored in commercial liquid detergents.

15 Claims, 14 Drawing Sheets

OTHER PUBLICATIONS

L. Kravetz, et al., "Effect of Surfactant Structure on Stability of Enzymes Formulated into Laundry Liquids," Journal of the American Oil Chemists' Society, vol. 62, No. 5, pp. 943-949 (1985).

Francis S. Markland, et al. "VII. Isolation of Cyanogen Bromide Peptides and the Complete Amino Sequence," The Journal of Biological Chemistry, vol. 242, No. 22, pp. 5198-5211 (1967).

Yuzura Suzuki, et al. "Purification and Characterization of *Bacillus Coagulans* oligo-1,6-glusosidase," Eur. J. Biochem., vol. 158, pp. 77-83 (1986).

Emil Smith, et al. "V. The Complete Sequence Comparison with Subtilisin BPNO Evolutionary Relationships", Journal of Biotechical Chemistry, vol. 243, No. 9, pp. 2182-2191 (1978).

M. Bae, Biological Abstracts vol. 90, No. 7, 1990: Abstract 79647.

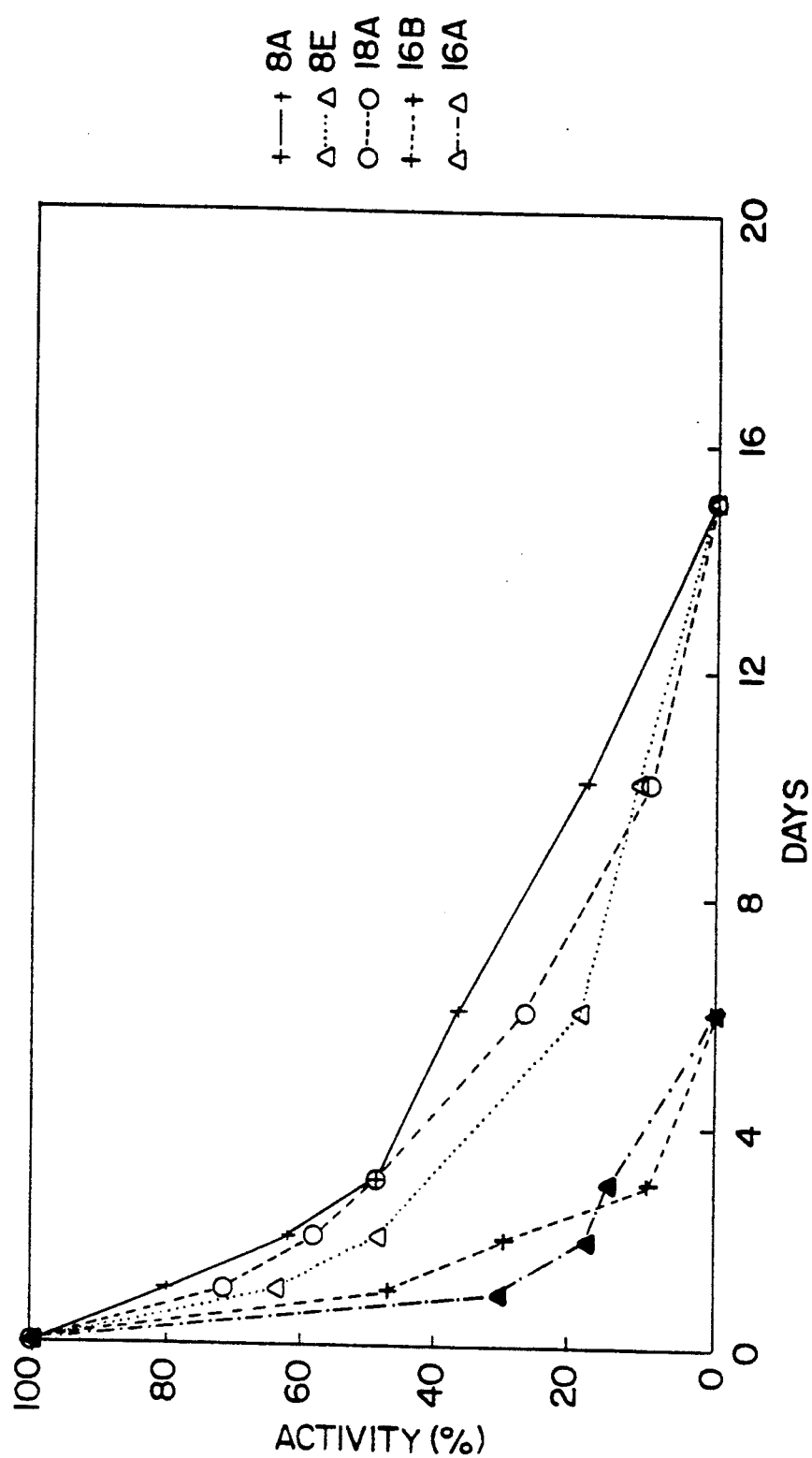

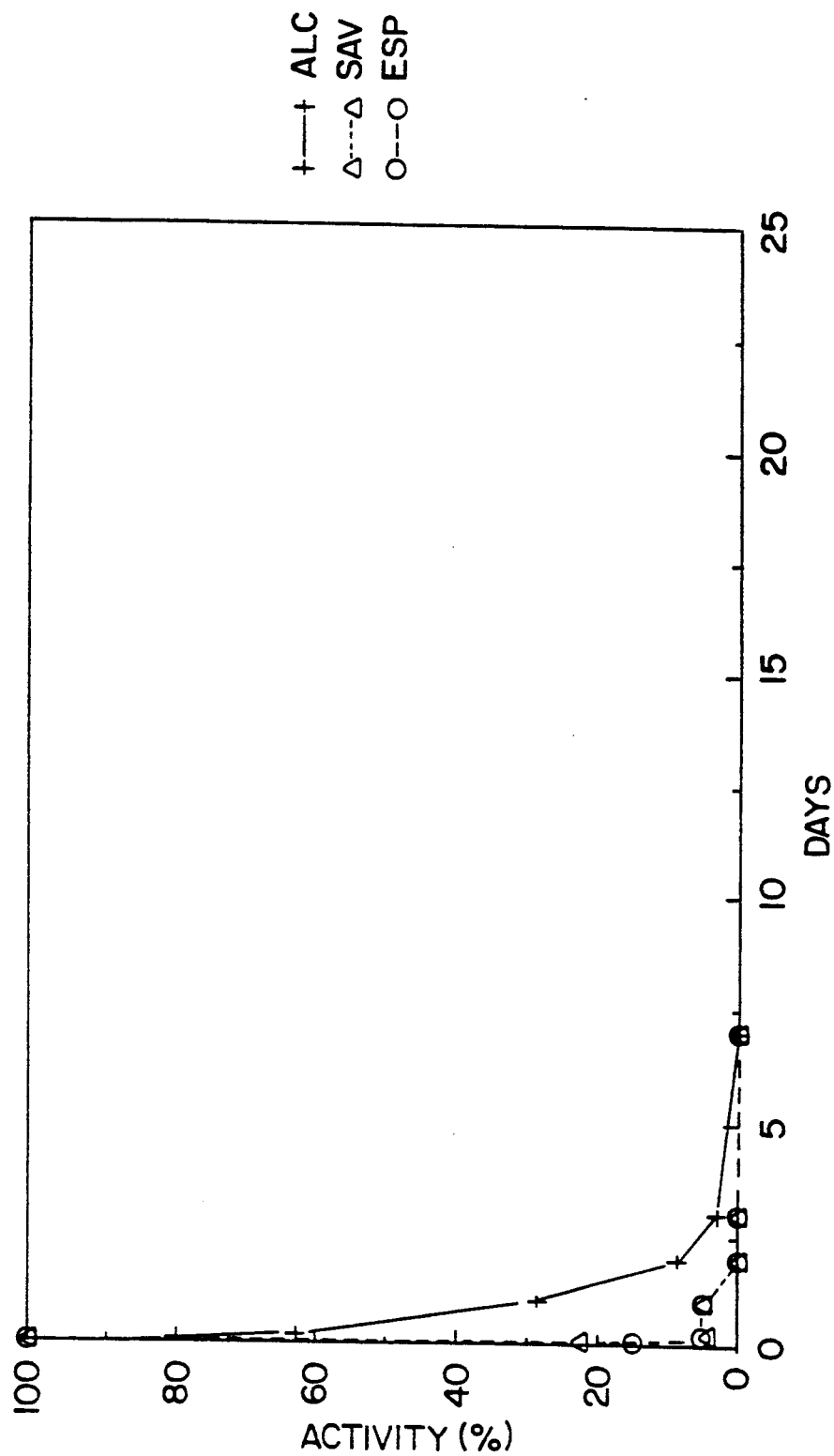

```
*    164A-1
a    Alkaline elastase:
b    Carlsberg:
c    subtilis:
d    amyloliquefaciens BPN':

1
*                                   -NVTNESKNI  VNSLGGSVHH  QYKYMDVLHV  SLPEKAAEAL
a    KDYLVGFKT—    EVMSQFVDQI      DGAEYSISSQ  AEDVEIDLLH  EFDFIPVLSV  ELDPEDVDAL
b    KYLI-GFKEQ    V                -KTASVKKDI  JKESGGKVDK  QFRIINAAKA  KLDKEALKEV
c    KDYIVGFKSG                    -MSSAKKKDV   ISEKGGKVQK  QFKYVNAAAA  TLDEKAVKEL
d    KKYIVGFKQT    MSA              -MSAKKKDV   ISEKGGKVQK  QFKYVDAASA  TLNEKAVKEL
     KKYIVGFKQT    MST 10          20          30
*    KNNPNNAEVD    LDAEVQAF         AQTTPWGITH   INAHKAHSSS  VTGSGVKVAV  LDTGIDASHP
a    ELDPAIAYIE    EDAEVTTM        -QTVPWGINR   VQAPIAQSRG  FTGTGVRVAV  LDTGI-SNHA
b    KNDPDVAYVE    EDHVAHAL         AQTVPYGIPL   IKADKVQAQG  FKGANVKVAV  LDTGIQASHP
c    KKDPSVAYVE    EDHIAHEY         AQSVPYGISQ   IKAPALHSQG  YTGSNVKVAV  IDSGIDSSHP
d    KKDPSVAYVE    EDHVAHAY         AQSVPYGVSQ   IKAPALHSQG  YTGSNVKVAV  IDSGIDSSHP 40            50               60           70          80          90
*    DLNVLGGASF    ISGEPNALVD       TNGHGTHVAG   TVAALNNTIG  VVGVAYNADL  YANKVLSASG
a    DLRIRGGASF    VPGE-PNISD       GNGHGTQVAG   TIAALNNSIG  VLGVAPNVDL  YGVKVLGASG
b    DLNVVGGASF    VAGEA-YNTD       GNGHGTHVAG   TVAALDNTTG  VLGVAPSVSL  YAVKVLNSSG
c    DLNVRGGASF    VPSETNPYQD       GSSHGTHVAG   TIAALNNSIG  VLGVSPSASL  YAVKVLDSTG
d    DLKVAGGASM    VPSETNPFQD       NNSHGTHVAG   TVAALNNSIG  VLGVAPSASL  YAVKVLGADG
```

FIG. 9A

```
            100              110              120              130              140              150
            |                |                |                |                |                |
*   SGTLSGIAGG      VEWAIANNMD       VINMSLGGSS       GSTALKQAVD       NAYASGIVVV       AAAGNSGTRG
a   SGSISGIAQG      LQWAANNGMH       IANMSLGSSA       GSATMEQAVN       QATASGVLVV       AASGNSGAGN
b   SGTYSGIVSG      IEWATTNGMD       VINMSLGGPS       GSTAMKQAVD       NAYARGVVVV       AAAGNSGSSG
c   SGQYSWIING      IEWAISNNMD       VINMSLGGPT       GSTALKTVVD       KAVSSGIVVA       AAGNEGSSG
d   SGQYSWIING      IEWAIANNMD       VINMSLGGPS       GSAALKAAVD       KAVASGVVVV       AAAGNQGTSG 160              170              180              190              200              210
            |                |                |                |                |                |
*   RQNTMGYPAR      YSSVIAVGAV       DSNNNRASFS       SVGAELEVMA       PGVSVLSTVP       GGGYASYNGT
a   ——VGFPAR        YANAMAVGAT       DQNNNRATFS       QYGAGLDIVA       PGVGVQSTVP       GNGYASFNGT
b   NTNTIGYPAK      YDSVIAVGAV       DSNSNRASFS       SVGAELEVMA       PGAGVYSTYP       TSTYATLNGT
c   STSTVGYPAK      YPSTIAVGAV       NSSNQRASFS       SAGSELDVMA       PGVSIQSTLP       GGTYGAYNGT
d   SSSTVGYPGK      YPSVIAVGAV       DSSNQRASFS       SVGPELDVMA       PGVSIQSTLP       GNKYGAYNGT 220              230              240              250              260              270
            |                |                |                |                |                |
*   SMASPHVAGA      AALIKAKYPS       LSASQIRDRL       RNTATYLGDP       FYYGNGVINV       ERALQ
a   SMATPHVAGV      AALVKQKNPS       WSNVQIRNHL       KNTATNLGNT       TQFGSGLVNA       EAATR
b   SMATPHVAGA      AALILSKHPN       LSASQVRNRL       SSTATYLGSS       FYYGKGLINV       EAAAQ
c   SMATPHVAGA      AALILSKHPT       WTNAQVRDRL       ESTATYLGNS       FYYGKGLINV       QAAAQ
d   SMASPHVAGA      AALILSKHPN       WTNTQVRSSL       ENTTTKLGDS       FYYGKGLINV       QAAAQ
```

FIG. 9B

```
         20                  40                  60                  80                 100
TCTAGTATTTGTTGTTTTAC CTGCTGTTTTAAGGAGCTA CCTTTTGGTGATTTTCTT  AGTTCTATTTTAATACTAT TACTTTTGCTACACTTACT
AGATCATAAACAACAAATG  GACGACAAAAATTGCTCGAT GGAAAACCACTAAAAGAA TCAAGATAAAATTATGATA ATGAAAAACGATGTGAATGA 120                 140                 160                 180                 200
TCTGCTTTTTCCATTTTAGA AATAATTGTAGCAGCTTTAA TCAAAGGGGATAAAGAAAAG AGGAAAAGACTTTCATGGAT AACTGGTAGCCTTATTTTC
AGACGAAAAAGGTAAAATCT TTATTAACATCGTCGAAATT AGTTTCCCCTATTTCTTTTC TCCTTTTCTGAAAGTACCTA TTGACCATCGGAATAAAAG 220                 240                 260                 280                 300
TTATAGGAATCCCATCTGCA TTATCTTTCGGGTATTCTTC ACATATTACTTATTAGATC GCACCATTTTTGATGTAGCA GATTTTTTGTAAGTAATGT
AATATCCTTAGGGTAGACGT AATAGAAAGCCATAAGAAG TGTATAATGAAATAATCTAG CGTGGTAAAAACTACATCGT CTAAAAAAGCATTCATTACA 320                 340                 360                 380                 400
GGCACTGCGGCTTGGGAGCGTT ACTTATTCTATTTTTGTAG GGTACAGGGTAGCGATAGAAT ATTTTAGAAGATGAGTTTT CCAAGGGTCAAAAGCTAAA
CCGTGACGCCGAACCTCGCAA TGAATAAAGATAAAAACATC CCATGTCCCATGCTATCTTA TAAAATCTTCTACTCAAAAA GGTTCCCAGTTTTCGATTT 420                 440                 460                 480                 500
AGTCCTTATTTACTATTTGG TATTTTACAATTAGATATAT TGTTCCAGTTGGGATAGCGG TGTATTTATTTATTCCATC GGAAATTTCGATTAACTAAA
TCAGGAATAAATGATAAACC ATAAAAATGTTAATCTATATA ACAAGGTCAACCCTATCGCC AGCATAAATAAGGTAG CCTTTAAAGCTAATTGATTT
```

FIG. 10A

```
           620                640                 660                    680                    700
CTTACTCTATTTGCACCT   TACTTTCCAATAGGTAAAA   TAGTTTTCTATGCTAATAT   CTTGGGTAATAGTTCTAATG   TTTAGAATTATTAAAAATG
GAAATGAGATAAACGTGGA  ATGAAAGGGTTATCCATTTT  ATCCAAAAGATACGATTATA  GAACCCATTATCAAGATTAC   AAATCTTAATAATTTTTTAC 720                740                  760                  780                    800
CCAAGGAGTGGTGTAGTGTT  GAAGAAGTGGATGAAAGTAT  TATCAGTAGTTTGTATTACG  ATTTTAACTTTATCATTAGC   AATCGGTTCTGTGAAGCAA
GGTTCCTCACCACATCACAA  CTTCTTCACCTACTTTCATA  ATAGTCATCAAACATAATGC  TAAAATTGAAATAGTAATCG   TTAGCCAAGACAGCTTCGTT
     ValLeu LysLys TrpMet LysVal LeuSer ValVal CysIle Thr   IleLeuThr LeuSer LeuAla    IleGly SerValGluAla
                                  a  PRE-PRO 164A-1                                    a 820                 840                   860                   880                    900
GTGGGAAAAATGCTGAAATT  AAGAAAGATTACTTAGTTGG  TTTTAAAACGAATGTAACCA  ATGAATCTAAAAATATAGTA   AACTCACTAGGTGGAAGTGT
CACCCTTTTTACGACTTTAA  TTCTTTCTAATGAATCAACC  AAAATTTGCTTACATTGGT   TACTTAGATTTTTATATCAT   TTGAGTGATCCACCTTCACA
SerGlyLysAsnAlaGluIle LysLysAspTyrLeuValGly PheLysThrAsnValThr    AsnGluSerLysAsnIleVal  AsnSerLeuGlyGlySerVal
           a  PRE-PRO 164A-1                             a 920                 940                   960                   980                   1000
ACATCATCAATATAAGTATA  TGGACGTATTGCATGTATCT  CTCCCAGAAAAGCAGCAGA   AGCATTAAAAACAATCCGA    ATGTAGCATTTGTGATTTA
TGTAGTAGTTATATTCAT    ACCTGCATAACGTACATAGA  GAGGGTCTTTTTCGTCGTCT  TCGTAATTTTTGTTAGGCT    TACATCGTAAACAGCTAAAT
HisHisGlnTyr LysTyr   MetAspValLeuHisValSer LeuProGluLysAlaAlaGlu AlaLeuLysAsnAsnPro     AsnValAlaPheValAspLeu
                                                      a  PRE-PRO 164A-1                       a
```

FIG. IOB

```
                                                                                                      1100
      1020                    1040                    1060                    1080                     ↓
       ↓                       ↓                       ↓                       ↓
GATGCTGAAGTTCAAGCATT  TGCACAAACTACTCCTTGGG  GAATTACGCATATTAATGCG  CATAAAGCACACAGCTCTAG  CGTTACTGGATCTGGTGTGA
CTACGACTTCAAGTTCGTAA  ACGTGTTTGATGAGGAACCC  CTTAATGCGTATAATTAGCG  GTATTTCGTGTGTCGAGATC  GCAATGACCTAGACCACACT
AspAla GluValGln AlaPhe                    AlaGlnThrThr ProTrp  Gly Ile ThrHis Ile AsnAla HisLysAla HisSerSer  ValThr Gly SerGly Val
 PRE-PRO 164A-1      a                                           b                      164A-1 MATURE PROTEIN                       b 1200
      1120                    1140                    1160                    1180                     ↓
       ↓                       ↓                       ↓                       ↓
AAGTTGCCGTTCTTGATACT  GGAATTGATGCTAGTCATCC  AGATTTAAATGTAAAAGGTG  AGATTTTATCTCTGGT  GAGCAAGTTGACTCACTTGTTGA
TTCAACGGCAAGAACTATGA  CCTTAACTACGATCAGTAGG  TCTAAATTTACATTTTCCAC  CTCGTTCAAAATAGAGACCA  CTCGGGTTACGTGAACAACT
LysValAla ValLeuAspThr Gly Ile AspAlaSerHisPro  AspLeuAsnVal LysGly  Gly AlaSerPhe Ile SerGly  GluPro AsnAla LeuVal Asp
                      b                      164A-1 MATURE PROTEIN                       b 1300
      1220                    1240                    1260                    1280                     ↓
       ↓                       ↓                       ↓                       ↓
TACAAAATGGTCATGGTACAC  ATGTAGCTGGTACGACCATGG  GCATTAAACAATACAATCGG  TGTTGTAGGAGTTGCATACA  ATGCAGATTATATGCGTT
ATGTTTACCAGTACCATGTG  TACATCGACCATGCCATACC  CGTAATTTGTTATGTTAGCC  ACAACATCCTCAACGTATGT  TACGTCTAAATATACGACAA
ThrAsnGly HisGly Thr  HisValAla Gly Thr  HisValAla Gly Thr  Val Ala Gly  Val ValGly ValAlaTyr  AsnAla AspLeuTyr AlaVal
                      b                      164A-1 MATURE PROTEIN                       b
```

FIG. 10C

```
      1320              1340              1360              1380              1400
AAAGTATTAAGTGCTTCAGG AAGTGGAACGTTAAGTGGAA TTGCTCAAGGTGTTGAATGG GCAATTGCTAATAATATGGA TGTAATTAACATGAGTCTTG
TTTCATAATTCACGAAGTCC TTCACCTTGCAATTCACCTT AACGAGTTCCACAACTTACC CGTTAACGATTATTATACCT ACATTAATTGTACTCAGAAC
LysVal LeuSer Ala SerGly  SerGly ThrLeuSerGly  IleAla Gln GlyValGluTrp  AlaIle AlaAsnAsnMetAsp  ValIle AsnMet SerLeu
         b                                     164A-1 MATURE PROTEIN                                              b 1420              1440              1460              1480              1500
GTGGGAGTTCTGGATCTACA GCATTAAAGCAAGCTGTTGA TAATGCTTATGCTAGCGGAA TTGTTGTAGTAGCAGCGGCT GGTAATAGCGGAACAAGAGG
CACCCTCAAGACCTAGATGT CGTAATTTCGTTCGACAACT ATTACGAATACGATCGCCTT AACAACATCATCGTCGCCGA CCATTATCGCCTTGTTCTCC
GlyGly SerSerGly SerThr  AlaLeuLys GlnAlaValAsp  AsnAlaTyrAla SerGly  IleValVal ValAlaAlaAla  GlyAsnSer GlyThrArgGly
         b                                     164A-1 MATURE PROTEIN                                              b
```

FIG. 10 D

```
                1540                    1560                   1580                    1600
AAGACAGAACACAATGGGCT  ACCCAGCAAGATATAGTTCA  GTAATTGCTGTTGGTGCGGT  AGACTCAAATAACAATCGTG  CATCATTCTCTAGCGTAGGT
TTCTGTCTTGTGTTACCGA   TGGGTCGTTCTATATCAAGT  CATTAACGACAACCACCGCCA TCTGAGTTTATTGTTAGCAC  GTAGTAAGAGATCGCATCCA
Arg Gln Asn Thr Met Gly  Tyr Pro Ala Arg Tyr Ser Ser  Val Ile Ala Val Gly Val  Asp Ser Asn Asn Arg  Ala Ser Phe Ser Val Gly
                              164A-1 MATURE PROTEIN                                                       b 1620                    1640                   1660                    1680                    1700
GCTGAACTAGAAGTAATGGC  TCCTGGTGTAAGTGTTTTAA  GTACAGTACCAGGTGGTGGT  TATGCTTCTTATAATGGAAC  ATCAATGGCTTCTCCACATG
CGACTTGATCTTCATTACCG  AGGACCACATTCACAAAATT  CATGTCATGGTCCACCACCA  ATACGAAGAATATTACCTTG  TAGTTACCGAAGAGGTGTAC
Ala Glu Leu Glu Val Met Ala  Pro Gly Val Ser Val Leu  Ser Thr Val Pro Gly Gly Gly  Tyr Ala Ser Tyr Asn Gly Thr  Ser Met Ala Ser Pro His
                                                          164A-1 MATURE PROTEIN                                          b 1720                    1740                   1760                    1780                    1800
TAGCAGGAGCAGCAGCTTTA  ATTAAAGCTAAATACCCAAG  TCTTTCTGCTTCGCAAATTC  GTGATAGATTAAGAAAACACA GCTACTTACTTAGGTGATCC
ATCGTCCTCGTCGTCGAAAT  TAATTTCGATTTATGGGTTC  AGAAAGACGAAGCGTTTAAG  CACTATCTAATTCTTGTGT   CGATGAATGAATCCACTAGG
Val Ala Gly Ala Ala Leu  Ile Lys Ala Lys Tyr Pro Ser  Leu Ser Ala Ser Gln Ile  Arg Asp Arg Leu Arg Asn Thr  Ala Thr Tyr Leu Gly Asp Pro
                                                          164A-1 MATURE PROTEIN                                          b 1820                    1840                   1860
ATTCTATTATGGAAACGGAG  TTATAAATGTAGAGAGAGCA  TTACAATAATAAATAATAAT  TGTAAGC
TAAGATAATACCTTTGCCTC  AATATTTACACATCTCTCGT  AATGTTATTATTTATTATTA  ACATTCG
Phe Tyr Tyr Gly Asn Gly  Val Ile Asn Val Glu Arg Ala  Leu Gln
      164A-1 MATURE PROTEIN                              b
```

FIG. IOE

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 1867 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( B ) STRAIN: 164A-1

( i x ) FEATURE:
        ( A ) NAME/KEY: CDS
        ( B ) LOCATION: 716..1849
        ( D ) OTHER INFORMATION: /product="mature protein of
            164A-1"

( i x ) FEATURE:
        ( A ) NAME/KEY: sigpeptide
        ( B ) LOCATION: 716..1021

( i x ) FEATURE:
        ( A ) NAME/KEY: matpeptide
        ( B ) LOCATION: 1022..1846

( x i ) SEQUENCE DESCRIPTION: SEQ ID NO:1:

```
TCTAGTATTT  GTTGTTTTAC  CTGCTGTTTT  TAACGAGCTA  CCTTTTGGTG  GATTTTTCTT      60

AGTTCTATTT  TTAATACTAT  TACTTTTTGC  TACACTTACT  TCTGCTTTTT  CCATTTTAGA     120

AATAATTGTA  GCAGCTTTAA  TCAAAGGGGA  TAAAGAAAAG  AGGAAAAGAC  TTTCATGGAT     180

AACTGGTAGC  CTTATTTTTC  TTATAGGAAT  CCCATCTGCA  TTATCTTTCG  GTATTCTTTC     240

ACATATTACT  TTATTAGATC  GCACCATTTT  TGATGTAGCA  GATTTTTTCG  TAAGTAATGT     300

GGCACTGCGC  TTGGAGCGTT  ACTTATTTCT  ATTTTTGTAG  GGTACAGGGT  ACGATAGAAT     360

ATTTTAGAAG  ATGAGTTTTT  CCAAGGGTCA  AAAGCTAAAA  AGTCCTTATT  TACTATTTGG     420

TATTTTACAA  TTAGATATAT  TGTTCCAGTT  GGGATAGCGG  TCGTATTTAT  TTATTCCATC     480

GGAAATTTCG  ATTAACTAAA  AACACTGAAG  CCTTGCTTCA  GTTTTTTTTA  TTAGATTTTC     540

AAGTTATTTC  TTTTTATTAC  ATTTATTACT  ATTGGGAAAA  TACATACAAC  AAAATGATTT     600

CTTTACTCTA  TTTTGCACCT  TACTTTCCCA  ATAGGTAAAA  TAGGTTTTCT  ATGCTAATAT     660

CTTGGGTAAT  AGTTCTAATG  TTTAGAATTA  TTAAAAAATG  CCAAGGAGTG  GTGTA  GTG     718
                                                                    Val
                                                                    -102

TTG  AAG  AAG  TGG  ATG  AAA  GTA  TTA  TCA  GTA  GTT  TGT  ATT  ACG  ATT  TTA      766
Leu  Lys  Lys  Trp  Met  Lys  Val  Leu  Ser  Val  Val  Cys  Ile  Thr  Ile  Leu
     -100                -95                      -90

ACT  TTA  TCA  TTA  GCA  ATC  GGT  TCT  GTC  GAA  GCA  AGT  GGG  AAA  AAT  GCT      814
Thr  Leu  Ser  Leu  Ala  Ile  Gly  Ser  Val  Glu  Ala  Ser  Gly  Lys  Asn  Ala
-85                 -80                      -75                      -70
```

```
GAA ATT AAG AAA GAT TAC TTA GTT GGT TTT AAA ACG AAT GTA ACC AAT     862
Glu Ile Lys Lys Asp Tyr Leu Val Gly Phe Lys Thr Asn Val Thr Asn
            -65             -60                     -55

GAA TCT AAA AAT ATA GTA AAC TCA CTA GGT GGA AGT GTA CAT CAT CAA     910
Glu Ser Lys Asn Ile Val Asn Ser Leu Gly Gly Ser Val His His Gln
        -50             -45                     -40

TAT AAG TAT ATG GAC GTA TTG CAT GTA TCT CTC CCA GAA AAA GCA GCA     958
Tyr Lys Tyr Met Asp Val Leu His Val Ser Leu Pro Glu Lys Ala Ala
    -35             -30                     -25

GAA GCA TTA AAA AAC AAT CCG AAT GTA GCA TTT GTC GAT TTA GAT GCT    1006
Glu Ala Leu Lys Asn Asn Pro Asn Val Ala Phe Val Asp Leu Asp Ala
-20             -15                     -10

GAA GTT CAA GCA TTT GCA CAA ACT ACT CCT TGG GGA ATT ACG CAT ATT    1054
Glu Val Gln Ala Phe Ala Gln Thr Thr Pro Trp Gly Ile Thr His Ile
-5              1               5                   10

AAT GCG CAT AAA GCA CAC AGC TCT AGC GTT ACT GGA TCT GGT GTG AAA    1102
Asn Ala His Lys Ala His Ser Ser Ser Val Thr Gly Ser Gly Val Lys
            15              20                  25

GTT GCC GTT CTT GAT ACT GGA ATT GAT GCT AGT CAT CCA GAT TTA AAT    1150
Val Ala Val Leu Asp Thr Gly Ile Asp Ala Ser His Pro Asp Leu Asn
        30              35                  40

GTA AAA GGT GGA GCA AGT TTT ATC TCT GGT GAG CCC AAT GCA CTT GTT    1198
Val Lys Gly Gly Ala Ser Phe Ile Ser Gly Glu Pro Asn Ala Leu Val
    45              50                  55

GAT ACA AAT GGT CAT GGT ACA CAT GTA GCT GGT ACG GTA GCT GCA TTA    1246
Asp Thr Asn Gly His Gly Thr His Val Ala Gly Thr Val Ala Ala Leu
60              65                  70                      75

AAC AAT ACA ATC GGT GTT GTA GGT GTT GCA TAC AAT GCA GAT TTA TAT    1294
Asn Asn Thr Ile Gly Val Val Gly Val Ala Tyr Asn Ala Asp Leu Tyr
            80              85                  90

GCT GTT AAA GTA TTA AGT GCT TCA GGA AGT GGA ACG TTA AGT GGA ATT    1342
Ala Val Lys Val Leu Ser Ala Ser Gly Ser Gly Thr Leu Ser Gly Ile
        95              100                 105

GCT CAA GGT GTT GAA TGG GCA ATT GCT AAT AAT ATG GAT GTA ATT AAC    1390
Ala Gln Gly Val Glu Trp Ala Ile Ala Asn Asn Met Asp Val Ile Asn
    110             115                 120

ATG AGT CTT GGT GGG AGT TCT GGA TCT ACA GCA TTA AAG CAA GCT GTT    1438
Met Ser Leu Gly Gly Ser Ser Gly Ser Thr Ala Leu Lys Gln Ala Val
125             130                 135

GAT AAT GCT TAT GCT AGC GGA ATT GTT GTA GTA GCA GCG GCT GGT AAT    1486
Asp Asn Ala Tyr Ala Ser Gly Ile Val Val Val Ala Ala Ala Gly Asn
140             145                 150                     155

AGC GGA ACA AGA GGA AGA CAG AAC ACA ATG GGC TAC CCA GCA AGA TAT    1534
Ser Gly Thr Arg Gly Arg Gln Asn Thr Met Gly Tyr Pro Ala Arg Tyr
            160             165                 170

AGT TCA GTA ATT GCT GTT GGT GCG GTA GAC TCA AAT AAC AAT CGT GCA    1582
Ser Ser Val Ile Ala Val Gly Ala Val Asp Ser Asn Asn Asn Arg Ala
        175             180                 185

TCA TTC TCT AGC GTA GGT GCT GAA CTA GAA GTA ATG GCT CCT GGT GTA    1630
Ser Phe Ser Ser Val Gly Ala Glu Leu Glu Val Met Ala Pro Gly Val
    190             195                 200

AGT GTT TTA AGT ACA GTA CCA GGT GGT GGT TAT GCT TCT TAT AAT GGA    1678
Ser Val Leu Ser Thr Val Pro Gly Gly Gly Tyr Ala Ser Tyr Asn Gly
205             210                 215

ACA TCA ATG GCT TCT CCA CAT GTA GCA GGA GCA GCA GCT TTA ATT AAA    1726
Thr Ser Met Ala Ser Pro His Val Ala Gly Ala Ala Ala Leu Ile Lys
220             225                 230                     235

GCT AAA TAC CCA AGT CTT TCT GCT TCG CAA ATT CGT GAT AGA TTA AGA    1774
Ala Lys Tyr Pro Ser Leu Ser Ala Ser Gln Ile Arg Asp Arg Leu Arg
            240                 245                 250

AAC ACA GCT ACT TAC TTA GGT GAT CCA TTC TAT TAT GGA AAC GGA GTT    1822
```

| | | | | | | | | | | | | | |
|---|---|---|---|---|---|---|---|---|---|---|---|---|---|
|Asn|Thr|Ala|Thr<br>255|Tyr|Leu|Gly|Asp|Pro<br>260|Phe|Tyr|Tyr|Gly|Asn|Gly<br>265|Val|

```
ATA AAT GTA GAG AGA GCA TTA CAA TAATAAATAA TAATTGTAAG C            1867
Ile Asn Val Glu Arg Ala Leu Gln
        270             275
```

( 2 ) INFORMATION FOR SEQ ID NO:2:

( i ) SEQUENCE CHARACTERISTICS:
        ( A ) LENGTH: 377 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Val  Leu  Lys  Lys  Trp  Met  Lys  Val  Leu  Ser  Val  Val  Cys  Ile  Thr  Ile
-102      -100                -95                     -90

Leu  Thr  Leu  Ser  Leu  Ala  Ile  Gly  Ser  Val  Glu  Ala  Ser  Gly  Lys  Asn
     -85                -80                     -75

Ala  Glu  Ile  Lys  Lys  Asp  Tyr  Leu  Val  Gly  Phe  Lys  Thr  Asn  Val  Thr
-70                -65                     -60                          -55

Asn  Glu  Ser  Lys  Asn  Ile  Val  Asn  Ser  Leu  Gly  Gly  Ser  Val  His  His
               -50                     -45                          -40

Gln  Tyr  Lys  Tyr  Met  Asp  Val  Leu  His  Val  Ser  Leu  Pro  Glu  Lys  Ala
          -35                     -30                          -25

Ala  Glu  Ala  Leu  Lys  Asn  Asn  Pro  Asn  Val  Ala  Phe  Val  Asp  Leu  Asp
          -20                -15                          -10

Ala  Glu  Val  Gln  Ala  Phe  Ala  Gln  Thr  Thr  Pro  Trp  Gly  Ile  Thr  His
     -5                      1                    5                          10

Ile  Asn  Ala  His  Lys  Ala  His  Ser  Ser  Ser  Val  Thr  Gly  Ser  Gly  Val
               15                     20                          25

Lys  Val  Ala  Val  Leu  Asp  Thr  Gly  Ile  Asp  Ala  Ser  His  Pro  Asp  Leu
               30                     35                          40

Asn  Val  Lys  Gly  Gly  Ala  Ser  Phe  Ile  Ser  Gly  Glu  Pro  Asn  Ala  Leu
          45                     50                          55

Val  Asp  Thr  Asn  Gly  His  Gly  Thr  His  Val  Ala  Gly  Thr  Val  Ala  Ala
     60                     65                          70

Leu  Asn  Asn  Thr  Ile  Gly  Val  Val  Gly  Val  Ala  Tyr  Asn  Ala  Asp  Leu
75                     80                     85                          90

Tyr  Ala  Val  Lys  Val  Leu  Ser  Ala  Ser  Gly  Ser  Gly  Thr  Leu  Ser  Gly
               95                     100                         105

Ile  Ala  Gln  Gly  Val  Glu  Trp  Ala  Ile  Ala  Asn  Asn  Met  Asp  Val  Ile
               110                    115                         120

Asn  Met  Ser  Leu  Gly  Gly  Ser  Ser  Gly  Ser  Thr  Ala  Leu  Lys  Gln  Ala
          125                    130                         135

Val  Asp  Asn  Ala  Tyr  Ala  Ser  Gly  Ile  Val  Val  Ala  Ala  Ala  Gly
     140                    145                    150

Asn  Ser  Gly  Thr  Arg  Gly  Arg  Gln  Asn  Thr  Met  Gly  Tyr  Pro  Ala  Arg
155                     160                    165                         170

Tyr  Ser  Ser  Val  Ile  Ala  Val  Gly  Ala  Val  Asp  Ser  Asn  Asn  Asn  Arg
               175                               180                        185

Ala  Ser  Phe  Ser  Ser  Val  Gly  Ala  Glu  Leu  Glu  Val  Met  Ala  Pro  Gly
          190                         195                    200

Val  Ser  Val  Leu  Ser  Thr  Val  Pro  Gly  Gly  Gly  Tyr  Ala  Ser  Tyr  Asn
     205                         210                    215

Gly  Thr  Ser  Met  Ala  Ser  Pro  His  Val  Ala  Gly  Ala  Ala  Ala  Leu  Ile
     220                    225                         230
```

```
Lys  Ala  Lys  Tyr  Pro  Ser  Leu  Ser  Ala  Ser  Gln  Ile  Arg  Asp  Arg  Leu
235                      240                 245                      250

Arg  Asn  Thr  Ala  Thr  Tyr  Leu  Gly  Asp  Pro  Phe  Tyr  Tyr  Gly  Asn  Gly
                    255                 260                      265

Val  Ile  Asn  Val  Glu  Arg  Ala  Leu  Gln
               270                 275
```

( 2 ) INFORMATION FOR SEQ ID NO:3:

( i ) SEQUENCE CHARACTERISTICS:
        ( A ) LENGTH: 378 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Bacillus
        ( B ) STRAIN: alkaline elastase ( x i ) SEQUENCE DESCRIPTION: SEQ ID NO:3:

```
Met  Asn  Lys  Lys  Met  Gly  Lys  Ile  Val  Ala  Gly  Thr  Ala  Leu  Ile  Ile
1                   5                   10                      15

Ser  Val  Ala  Phe  Ser  Ser  Ser  Ile  Ala  Gln  Ala  Ala  Glu  Glu  Ala  Lys
               20                  25                      30

Glu  Lys  Tyr  Leu  Ile  Gly  Phe  Lys  Glu  Gln  Glu  Val  Met  Ser  Gln  Phe
          35                       40                      45

Val  Asp  Gln  Ile  Asp  Gly  Ala  Glu  Tyr  Ser  Ile  Ser  Ser  Gln  Ala  Glu
     50                       55                      60

Asp  Val  Glu  Ile  Asp  Leu  Leu  His  Glu  Phe  Asp  Phe  Ile  Pro  Val  Leu
65                       70                      75                       80

Ser  Val  Glu  Leu  Asp  Pro  Glu  Asp  Val  Asp  Ala  Leu  Glu  Leu  Asp  Pro
               85                       90                      95

Ala  Ile  Ala  Tyr  Ile  Glu  Glu  Asp  Ala  Glu  Val  Thr  Thr  Met  Gln  Thr
                    100                      105                     110

Val  Pro  Trp  Gly  Ile  Asn  Arg  Val  Gln  Ala  Pro  Ile  Ala  Gln  Ser  Arg
               115                      120                     125

Gly  Phe  Thr  Gly  Thr  Gly  Val  Arg  Val  Ala  Val  Leu  Asp  Thr  Gly  Ile
     130                      135                     140

Ser  Asn  His  Ala  Asp  Leu  Arg  Ile  Arg  Gly  Gly  Ala  Ser  Phe  Val  Pro
145                      150                      155                     160

Gly  Glu  Pro  Asn  Ile  Ser  Asp  Gly  Asn  Gly  His  Gly  Thr  Gln  Val  Ala
                    165                      170                     175

Gly  Thr  Ile  Ala  Ala  Leu  Asn  Asn  Ser  Ile  Gly  Val  Leu  Gly  Val  Ala
               180                      185                     190

Pro  Asn  Val  Asp  Leu  Tyr  Gly  Val  Lys  Val  Leu  Gly  Ala  Ser  Gly  Ser
          195                      200                     205

Gly  Ser  Ile  Ser  Gly  Ile  Ala  Gln  Gly  Leu  Gln  Trp  Ala  Ala  Asn  Asn
     210                      215                     220

Gly  Met  His  Ile  Ala  Asn  Met  Ser  Leu  Gly  Ser  Ser  Ala  Gly  Ser  Ala
225                      230                      235                     240

Thr  Met  Glu  Gln  Ala  Val  Asn  Gln  Ala  Thr  Ala  Ser  Gly  Val  Leu  Val
               245                      250                     255

Val  Ala  Ala  Ser  Gly  Asn  Ser  Gly  Ala  Gly  Asn  Val  Gly  Phe  Pro  Ala
          260                      265                     270

Arg  Tyr  Ala  Asn  Ala  Met  Ala  Val  Gly  Ala  Thr  Asp  Gln  Asn  Asn  Asn
     275                      280                     285

Arg  Ala  Thr  Phe  Ser  Gln  Tyr  Gly  Ala  Gly  Leu  Asp  Ile  Val  Ala  Pro
     290                      295                     300
```

-continued

| | | | | | | | | | | | | | | | |
|---|---|---|---|---|---|---|---|---|---|---|---|---|---|---|---|
| Gly | Val | Gly | Val | Gln | Ser | Thr | Val | Pro | Gly | Asn | Gly | Tyr | Ala | Ser | Phe |
| 305 | | | | 310 | | | | | 315 | | | | | | 320 |
| Asn | Gly | Thr | Ser | Met | Ala | Thr | Pro | His | Val | Ala | Gly | Val | Ala | Ala | Leu |
| | | | | 325 | | | | | 330 | | | | | 335 | |
| Val | Lys | Gln | Lys | Asn | Pro | Ser | Trp | Ser | Asn | Val | Gln | Ile | Arg | Asn | His |
| | | | 340 | | | | | 345 | | | | 350 | | | |
| Leu | Lys | Asn | Thr | Ala | Thr | Asn | Leu | Gly | Asn | Thr | Thr | Gln | Phe | Gly | Ser |
| | | 355 | | | | 360 | | | | | 365 | | | | |
| Gly | Leu | Val | Asn | Ala | Glu | Ala | Ala | Thr | Arg | | | | | | |
| | 370 | | | | 375 | | | | | | | | | | |

( 2 ) INFORMATION FOR SEQ ID NO:4:

( i ) SEQUENCE CHARACTERISTICS:
        ( A ) LENGTH: 378 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Bacillus
        ( B ) STRAIN: Carlsberg ( x i ) SEQUENCE DESCRIPTION: SEQ ID NO:4:

| | | | | | | | | | | | | | | | |
|---|---|---|---|---|---|---|---|---|---|---|---|---|---|---|---|
| Met | Met | Arg | Lys | Lys | Ser | Phe | Trp | Leu | Gly | Met | Leu | Thr | Ala | Phe | Met |
| 1 | | | | 5 | | | | | 10 | | | | | 15 | |
| Leu | Val | Phe | Thr | Met | Ala | Phe | Ser | Asp | Ser | Ala | Ser | Ala | Ala | Gln | Pro |
| | | | 20 | | | | | 25 | | | | | 30 | | |
| Ala | Lys | Asn | Val | Glu | Lys | Asp | Tyr | Ile | Val | Gly | Phe | Lys | Ser | Gly | Val |
| | | | 35 | | | | 40 | | | | | 45 | | | |
| Lys | Thr | Ala | Ser | Val | Lys | Lys | Asp | Ile | Lys | Glu | Ser | Gly | Gly | Lys | Val |
| | 50 | | | | | 55 | | | | | 60 | | | | |
| Asp | Lys | Gln | Phe | Arg | Ile | Ile | Asn | Ala | Ala | Lys | Ala | Lys | Leu | Asp | Lys |
| 65 | | | | | 70 | | | | | 75 | | | | | 80 |
| Glu | Ala | Leu | Lys | Glu | Val | Lys | Asn | Asp | Pro | Asp | Val | Ala | Tyr | Val | Glu |
| | | | | 85 | | | | | 90 | | | | | 95 | |
| Glu | Asp | His | Val | Ala | His | Ala | Leu | Ala | Gln | Thr | Val | Pro | Tyr | Gly | Ile |
| | | | 100 | | | | | 105 | | | | | 110 | | |
| Pro | Leu | Ile | Lys | Ala | Asp | Lys | Val | Gln | Ala | Gln | Gly | Phe | Lys | Gly | Ala |
| | | | 115 | | | | 120 | | | | | 125 | | | |
| Asn | Val | Lys | Val | Ala | Val | Leu | Asp | Thr | Gly | Ile | Gln | Ala | Ser | His | Pro |
| | 130 | | | | | 135 | | | | | 140 | | | | |
| Asp | Leu | Asn | Val | Val | Gly | Gly | Ala | Ser | Phe | Val | Ala | Gly | Glu | Ala | Tyr |
| 145 | | | | | 150 | | | | | 155 | | | | | 160 |
| Asn | Thr | Asp | Gly | Asn | Gly | His | Gly | Thr | His | Val | Ala | Gly | Thr | Val | Ala |
| | | | | 165 | | | | | 170 | | | | | 175 | |
| Ala | Leu | Asp | Asn | Thr | Thr | Gly | Val | Leu | Gly | Val | Ala | Pro | Ser | Val | Ser |
| | | | 180 | | | | | 185 | | | | | 190 | | |
| Leu | Tyr | Ala | Val | Lys | Val | Leu | Asn | Ser | Ser | Gly | Ser | Gly | Thr | Tyr | Ser |
| | | | 195 | | | | 200 | | | | | 205 | | | |
| Gly | Ile | Val | Ser | Gly | Ile | Glu | Trp | Ala | Thr | Thr | Asn | Gly | Met | Asp | Val |
| | 210 | | | | | 215 | | | | | 220 | | | | |
| Ile | Asn | Met | Ser | Leu | Gly | Gly | Pro | Ser | Gly | Ser | Thr | Ala | Met | Lys | Gln |
| 225 | | | | | 230 | | | | | 235 | | | | | 240 |
| Ala | Val | Asp | Asn | Ala | Tyr | Ala | Arg | Gly | Val | Val | Val | Ala | Ala | Ala | Ala |
| | | | | 245 | | | | | 250 | | | | | 255 | |
| Gly | Asn | Ser | Gly | Ser | Ser | Gly | Asn | Thr | Asn | Thr | Ile | Gly | Tyr | Pro | Ala |
| | | | 260 | | | | | 265 | | | | | 270 | | |

```
Lys  Tyr  Asp  Ser  Val  Ile  Ala  Val  Gly  Ala  Val  Asp  Ser  Asn  Ser  Asn
          275                280                          285

Arg  Ala  Ser  Phe  Ser  Ser  Val  Gly  Ala  Glu  Leu  Glu  Val  Met  Ala  Pro
     290                     295                294 300

Gly  Ala  Gly  Val  Tyr  Ser  Thr  Tyr  Pro  Thr  Ser  Thr  Tyr  Ala  Thr  Leu
305                      310                     315                          320

Asn  Gly  Thr  Ser  Met  Ala  Ser  Pro  His  Val  Ala  Gly  Ala  Ala  Ala  Leu
                    325                     330                               335

Ile  Leu  Ser  Lys  His  Pro  Asn  Leu  Ser  Ala  Ser  Gln  Val  Arg  Asn  Arg
               340                     345                     350

Leu  Ser  Ser  Thr  Ala  Thr  Tyr  Leu  Gly  Ser  Ser  Phe  Tyr  Tyr  Gly  Lys
          355                     360                     365

Gly  Leu  Ile  Asn  Val  Glu  Ala  Ala  Ala  Gln
     370                     375
```

( 2 ) INFORMATION FOR SEQ ID NO:5:

( i ) SEQUENCE CHARACTERISTICS:
      ( A ) LENGTH: 381 amino acids
      ( B ) TYPE: amino acid
      ( D ) TOPOLOGY: linear ( i i ) MOLECULE TYPE: protein ( v i ) ORIGINAL SOURCE:
      ( A ) ORGANISM: Bacillus
      ( B ) STRAIN: B. subtilis ( x i ) SEQUENCE DESCRIPTION: SEQ ID NO:5:

```
Met  Arg  Ser  Lys  Lys  Leu  Trp  Ile  Ser  Leu  Leu  Phe  Ala  Leu  Thr  Leu
1                   5                        10                          15

Ile  Phe  Thr  Met  Ala  Phe  Ser  Asn  Met  Ser  Ala  Gln  Ala  Ala  Gly  Lys
               20                     25                          30

Ser  Ser  Thr  Glu  Lys  Lys  Tyr  Ile  Val  Gly  Phe  Lys  Gln  Thr  Met  Ser
          35                       40                     45

Ala  Met  Ser  Ser  Ala  Lys  Lys  Lys  Asp  Val  Ile  Ser  Glu  Lys  Gly  Gly
     50                       55                     60

Lys  Val  Gln  Lys  Gln  Phe  Lys  Tyr  Val  Asn  Ala  Ala  Ala  Ala  Thr  Leu
65                       70                     75                          80

Asp  Glu  Lys  Ala  Val  Lys  Glu  Leu  Lys  Lys  Asp  Pro  Ser  Val  Ala  Tyr
               85                     90                          95

Val  Glu  Glu  Asp  His  Ile  Ala  His  Glu  Tyr  Ala  Gln  Ser  Val  Pro  Tyr
               100                    105                         110

Gly  Ile  Ser  Gln  Ile  Lys  Ala  Pro  Ala  Leu  His  Ser  Gln  Gly  Tyr  Thr
          115                    120                    125

Gly  Ser  Asn  Val  Lys  Val  Ala  Val  Ile  Asp  Ser  Gly  Ile  Asp  Ser  Ser
     130                      135                    140

His  Pro  Asp  Leu  Asn  Val  Arg  Gly  Gly  Ala  Ser  Phe  Val  Pro  Ser  Glu
145                      150                    155                         160

Thr  Asn  Pro  Tyr  Gln  Asp  Gly  Ser  Ser  His  Gly  Thr  His  Val  Ala  Gly
                    165                    170                    175

Thr  Ile  Ala  Ala  Leu  Asn  Asn  Ser  Ile  Gly  Val  Leu  Gly  Val  Ser  Pro
               180                    185                         190

Ser  Ala  Ser  Leu  Tyr  Ala  Val  Lys  Val  Leu  Asp  Ser  Thr  Gly  Ser  Gly
          195                    200                    205

Gln  Tyr  Ser  Trp  Ile  Ile  Asn  Gly  Ile  Glu  Trp  Ala  Ile  Ser  Asn  Asn
     210                      215                    220

Met  Asp  Val  Ile  Asn  Met  Ser  Leu  Gly  Gly  Pro  Thr  Gly  Ser  Thr  Ala
225                      230                    235                         240
```

```
Leu Lys Thr Val Val Asp Lys Ala Val Ser Ser Gly Ile Val Val Ala
            245             250             255

Ala Ala Ala Gly Asn Glu Gly Ser Ser Gly Ser Thr Ser Thr Val Gly
            260             265             270

Tyr Pro Ala Lys Tyr Pro Ser Thr Ile Ala Val Gly Ala Val Asn Ser
            275             280             285

Ser Asn Gln Arg Ala Ser Phe Ser Ser Ala Gly Ser Glu Leu Asp Val
            290             295             300

Met Ala Pro Gly Val Ser Ile Gln Ser Thr Leu Pro Gly Gly Thr Tyr
305             310             315             320

Gly Ala Tyr Asn Gly Thr Ser Met Ala Thr Pro His Val Ala Gly Ala
            325             330             335

Ala Ala Leu Ile Leu Ser Lys His Pro Thr Trp Thr Asn Ala Gln Val
            340             345             350

Arg Asp Arg Leu Glu Ser Thr Ala Thr Tyr Leu Gly Asn Ser Phe Tyr
            355             360             365

Tyr Gly Lys Gly Leu Ile Asn Val Gln Ala Ala Ala Gln
            370             375             380
```

(2) INFORMATION FOR SEQ ID NO:6:

(i) SEQUENCE CHARACTERISTICS:
  (A) LENGTH: 381 amino acids
  (B) TYPE: amino acid
  (D) TOPOLOGY: linear (ii) MOLECULE TYPE: protein (vi) ORIGINAL SOURCE:
  (A) ORGANISM: Bacillus
  (B) STRAIN: B. amyloliquefaciens (xi) SEQUENCE DESCRIPTION: SEQ ID NO:6:

```
Met Arg Gly Lys Lys Val Trp Ile Ser Leu Leu Phe Ala Leu Ala Leu
1               5                   10                  15

Ile Phe Thr Met Ala Phe Gly Ser Thr Ser Ser Ala Gln Ala Ala Gly
            20              25                  30

Lys Ser Asn Gly Glu Lys Lys Tyr Ile Val Gly Phe Lys Gln Thr Met
            35              40                  45

Ser Thr Met Ser Ala Ala Lys Lys Lys Asp Val Ile Ser Glu Lys Gly
    50              55                  60

Gly Lys Val Gln Lys Gln Phe Lys Tyr Val Asp Ala Ala Ser Ala Thr
65              70                  75                      80

Leu Asn Glu Lys Ala Val Lys Glu Leu Lys Lys Asp Pro Ser Val Ala
            85                  90              95

Tyr Val Glu Glu Asp His Val Ala Ala Ala Tyr Ala Gln Ser Val Pro
            100             105                 110

Tyr Gly Val Ser Gln Ile Lys Ala Pro Ala Leu His Ser Gln Gly Tyr
            115             120                 125

Thr Gly Ser Asn Val Lys Val Ala Val Ile Asp Ser Gly Ile Asp Ser
    130                 135                 140

Ser His Pro Asp Leu Lys Val Ala Gly Gly Ala Ser Met Val Pro Ser
145                 150                 155                 160

Glu Thr Asn Pro Phe Gln Asp Asn Asn Ser His Gly Thr His Val Ala
                165                 170                 175

Gly Thr Val Ala Ala Leu Asn Asn Ser Ile Gly Val Leu Gly Val Ala
            180                 185                 190

Pro Ser Ala Ser Leu Tyr Ala Val Lys Val Leu Gly Ala Asp Gly Ser
            195                 200                 205
```

-continued

| | | | | | | | | | | | | | | |
|---|---|---|---|---|---|---|---|---|---|---|---|---|---|---|
| Gly | Gln 210 | Tyr | Ser | Trp | Ile | Ile 215 | Asn | Gly | Ile | Glu | Trp 220 | Ala | Ile | Ala | Asn |
| Asn 225 | Met | Asp | Val | Ile | Asn 230 | Met | Ser | Leu | Gly | Gly 235 | Pro | Ser | Gly | Ser | Ala 240 |
| Ala | Leu | Lys | Ala | Ala 245 | Val | Asp | Lys | Ala | Val 250 | Ala | Ser | Gly | Val | Val 255 | Val |
| Val | Ala | Ala | Gly 260 | Asn | Gln | Gly | Thr | Ser 265 | Gly | Ser | Ser | Ser | Thr 270 | Val | Gly |
| Tyr | Pro | Gly 275 | Lys | Tyr | Pro | Ser | Val 280 | Ile | Ala | Val | Gly | Ala 285 | Val | Asp | Ser |
| Ser | Asn 290 | Gln | Arg | Ala | Ser | Phe 295 | Ser | Ser | Val | Gly | Pro 300 | Glu | Leu | Asp | Val |
| Met 305 | Ala | Pro | Gly | Val | Ser 310 | Ile | Gln | Ser | Thr | Leu 315 | Pro | Gly | Asn | Lys | Tyr 320 |
| Gly | Ala | Tyr | Asn | Gly 325 | Thr | Ser | Met | Ala | Ser 330 | Pro | His | Val | Ala | Gly 335 | Ala |
| Ala | Ala | Leu | Ile 340 | Leu | Ser | Lys | His | Pro 345 | Asn | Trp | Thr | Asn | Thr 350 | Gln | Val |
| Arg | Ser | Ser 355 | Leu | Glu | Asn | Thr | Thr 360 | Thr | Lys | Leu | Gly | Asp 365 | Ser | Phe | Tyr |
| Tyr | Gly 370 | Lys | Gly | Leu | Ile | Asn 375 | Val | Gln | Ala | Ala | Ala 380 | Gln | | | |

(2) INFORMATION FOR SEQ ID NO:7:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (vi) ORIGINAL SOURCE:
        (A) ORGANISM: Bacillus
        (B) STRAIN: B. licheniformis (xi) SEQUENCE DESCRIPTION: SEQ ID NO:7:

Ala  Gln  Thr  Val
1

(2) INFORMATION FOR SEQ ID NO:8:

(i) SEQUENCE CHARACTERISTICS:
        (A) LENGTH: 4 amino acids
        (B) TYPE: amino acid
        (D) TOPOLOGY: linear (ii) MOLECULE TYPE: protein (vi) ORIGINAL SOURCE:
        (A) ORGANISM: Bacillus
        (B) STRAIN: KP1239 from B. alcalophilis (xi) SEQUENCE DESCRIPTION: SEQ ID NO:8:

Ala  Gln  Ser  Val
1

ALKALINE PROTEASES STABLE IN HEAVY-DUTY DETERGENT LIQUIDS

BACKGROUND OF THE INVENTION

The present invention relates to a new group of alkaline proteases that are especially stable in the presence of detergents and bleaches. More particularly, the present invention relates to proteases that can be obtained, for example, from a particular class of soil bacteria and that are generally useful in heavy-duty detergent liquids (HDLs) which contain linear alkylbenzene sulfonate.

Alkaline proteases are commonly added to HDLs because of the ability of these enzymes to decompose proteinaceous stains. These enzymes perform at the high pHs which are beneficial to the detergency of the surfactants in these formulations. Exemplary of such alkaline proteases, which are generally from Bacillus species, are Esperase TM, Savinase TM and Alcalase TM from Novo Nordisk Bioindustrials Inc. and Maxatase TM and Maxacal TM from Gist-Brocades N.V. Although these enzymes have an optimal pH for activity of from 9 to 11, they rapidly lose their activity when stored at pH 10 to 11 in HDLs. This is especially true in HDLs with a high concentration of alkylbenzene sulfonates, such as linear alkylbenzene sulfonate (LAS). While anionic surfactants such as LAS provide excellent detergency at a low cost, they appear to be particularly detrimental to enzyme stability as compared to nonionic surfactants. See, for example, Kravetz et al., Am. Oil Chem. Soc. 62: 943 (1985).

Several patents relate to the stabilization of alkaline proteases in HDLs. Stabilization agents which have been used include formate and alcohols (U.S. Pat. No. 4,318,818), boric acid (U.S. Pat. No. 4,537,706), a combination of boron compounds, glycerin and a carboxylic acid (U.S. Pat. No. 4,900,475) and dicarboxylic acids and boric acid (GB patent application No. 21 26 242). But these stabilization systems do not sufficiently extend the lifetime of proteases, especially in high performance formulations having both a high pH and a high concentration of anionic surfactants.

Other patents relate to bacteria which produce alkaline proteases characterized by one or more properties. See, for example, U.S. Pat. Nos. 4,797,362, 4,771,003, 4,764,470, 3,838,009, 3,827,643 and 3,674,643. All of these patents relate to alkaline proteases obtained from specific bacterial strains, yet none discloses how any disclosed bacterial strain was isolated or how desirable strains other than those deposited might be reproducibly obtained to produce an alkaline protease with advantageous properties.

SUMMARY OF THE INVENTION

It is therefore an object of the present invention to provide a bacteria producing an enzyme that is stable for long periods of time in detergent liquids.

It is a further object of this invention to provide an enzyme that is stable when stored at high pH and that has excellent stability when stored in the presence of anionic surfactants such as LAS.

It is another object of this invention to provide an enzyme that has high stability and performance in the presence of bleaches.

It is yet another object of the invention to provide a reproducible process for isolating bacteria that produce enzymes that are stable in detergent liquids.

It is a further object of the invention to provide an isolated polynucleotide molecule that encodes an enzyme having the above-described stability characteristics.

In accomplishing these and other objects there has been provided, in accordance with one aspect of the present invention, a composition containing a recoverable amount of an enzyme with alkaline protease activity, said enzyme retaining at least 50% of its activity, according to the azocasein assay, after 12 hours at 52° C. in a stabilized aqueous solution having a pH of 9.8 and comprising 17.2 weight % of sodium $C_{11-5}$ alkylbenzene sulfonate, 5.2 weight % of a condensation product of one mole of $C_{12-15}$ linear alcohol and 7 moles of ethylene oxide, 5.8 weight % of sodium sulfate ester of the condensation product of one mole $C_{12-18}$ linear alcohol and 4 moles of ethylene oxide, 4.0 weight % of sodium xylene sulfonate, 5.5 weight % of sodium citrate, 1.4 weight % of triethanolamine, 1.4 weight % of monoethanolamine, 3.2 weight % of propylene glycol, 1.4 weight % of borax, 1.0 weight % of ethanol, 500 ppm $CaCl_2$, and the balance water. A bacterial culture consisting essentially of bacteria that produce an alkaline protease according to the invention is also provided, as well as an isolated polynucleotide molecule that encodes an enzyme with the aforementioned surprising stable alkaline protease activity.

A process for obtaining a bacterium that produces an alkaline protease that is stable at a pH greater than about 10 in the presence of linear alkylbenzene sulfonate is provided. In a first embodiment, this process comprises the steps of collecting soil from an alkaline environment which has been exposed to detergent contamination and selecting strains which have an alkaline protease that is stable in the presence of detergent. In a second embodiment, this process comprises the steps of collecting soil from an alkaline environment that has a pH greater than about 12 and selecting strains which have an alkaline protease that is stable in the presence of detergent.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description. By way of example, it is apparent that enzymes according to the present invention would be useful in cheese manufacture and as dehairing enzymes for leather preparation. In addition, in accordance with teachings of the present invention, oxidatively stable enzymes, in particular enzymes resistant to chlorine bleach and to perborate-containing detergent powders, can be readily obtained.

BRIEF DESCRIPTION OF THE DRAWINGS

FIG. 4A shows the stability of several proteases according to the present invention in Wisk TM at 38° C.

FIG. 4B shows the stability of Alcalase TM, Savinase TM and Esperase in Wisk at 38° C.

FIGS. 9A and 9B show the amino acid sequences for the protease of strain 164A-1 (Seq Il) No; 2) and four other proteases (SEQ Il) Nos. 3-6).

FIGS. 10A-10E show the DNA sequence (SEQ Il) NO: 1) encoding the amino acid sequence of the protease of strain 164A-1.

DETAILED DESCRIPTION OF PREFERRED EMBODIMENTS

Figure 1:
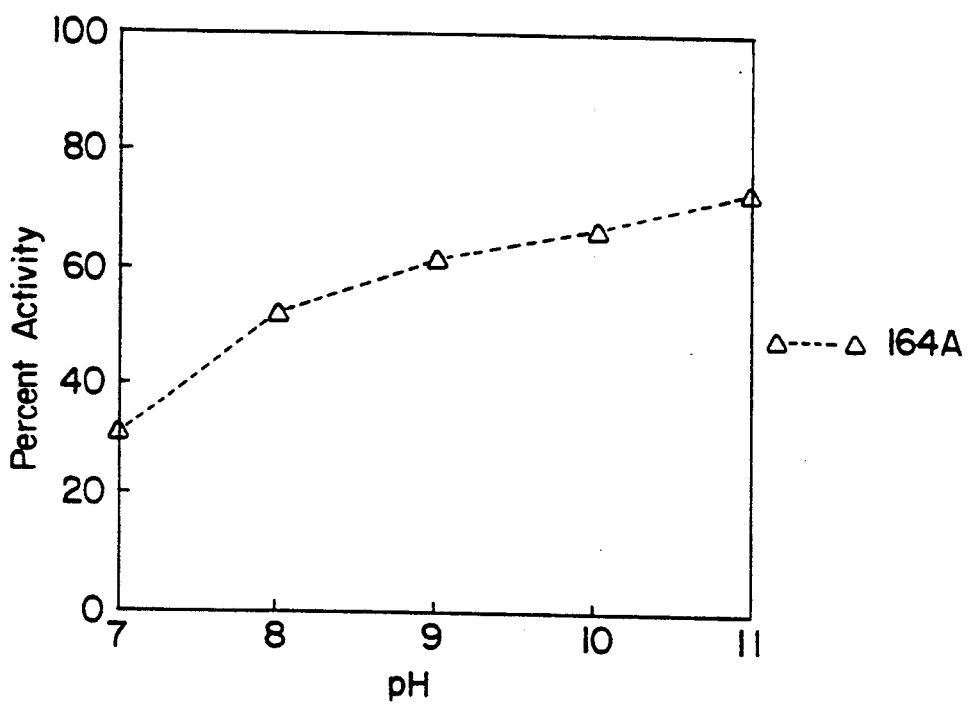
FIG. 1 shows the effect of pH on the activity of 164A-1, a protease within the present invention.

Bacteria having alkaline proteases that are stable in the presence of linear alkylbenzene sulfonates can be isolated from soil. A "stable" protease, in the context of the present invention, is at least twice as stable as Esperase TM in the detergent tests described herein. A protease according to the invention also retains at least fifty percent of its activity, according to the azocasein assay, after 12 hours at 52° C. in Formula A, a stabilized aqueous heavy-duty liquid detergent solution containing about 17 weight % LAS, as described herein. In this regard, "stabilized" refers to the incorporation of stabilizers of the type typically used in heavy-duty detergent liquids to prevent the rapid decomposition of enzymes. A particularly preferred protease according to the present invention retains at least fifty percent activity, according to the azocasein assay, after 12 days at 52° C. in Formula A.

The inventive protease can be obtained in recoverable amounts, pursuant to the present invention, in substantially pure form; that is, in a form such that the protein preparation migrates as a single band on an SDS-PAGE gel. Substantially pure protease according to the present invention can be obtained in recoverable amounts by isolating the protease produced by soil bacteria acquired as described herein, as well as by genetic-engineering techniques discussed in greater detail below. A "recoverable" amount in this regard means that the isolated amount of the protein is detectable by a methodology less sensitive than radiolabeling, such as an immunoassay, and can be subjected to further manipulations involving transfer of the protein per se into solution.

A bacterial culture according to the present invention consists essentially of one or more strains of bacteria that produce one or more proteases exhibiting the desired stability. That is, such a culture primarily contains one or more strains of bacteria which produce stable proteases and does not contain amounts of any bacteria sufficient to affect the properties of the culture. In particular, the culture must not contain any bacterial strains that interfere with production of stable protease by the strain or strains according to the invention, or that interfere with purification of the stable protease according to the invention from the culture. A preferred embodiment is a culture of strain that, by virtue of the selection procedure described herein, is a biologically pure culture.

According to one aspect of the present invention, soils are collected from sites characterized by soil properties indicative of the presence of the desired microflora. In particular, the soils of interest are highly alkaline, having a pH greater than 10 and preferably greater than 12. Generally, this level of alkalinity is the result of industrial activity at the site. Industrial sites characterized by alkaline soils include, for example, a cement plant, a tannery and a plant which produces synthetic surfactants. Strains of bacteria that produce an alkaline protease characterized by excellent stability in the presence of high pH and LAS can be reproducibly isolated from soils collected at such sites.

In addition to a highly alkaline pH, the soils of interest preferably are characterized further by contamination with detergents, in particular by LAS or by alkylate, the raw material from which LAS is produced. This contamination provides an additional selection pressure on the indigenous population of microorganisms in the soil, increasing the probability of finding bacteria having a protease that is stable in the presence of LAS. Soils from a site contaminated by LAS or alkylate are preferred, particularly those sites contaminated by LAS.

After a soil sample is collected, an enrichment protocol can be used to distinguish strains producing alkaline proteases stable in HDLs. A suspension of the soil can be plated onto a Petri dish containing an agar medium buffered to pH 10.5 and containing proteins as the source of carbon and nitrogen. This procedure results in the identification of strains that produce a protease enzyme.

A suitable alkaline agar media for suspending and diluting the soil samples comprises 0.5% yeast extract, 0.05% polypeptone, 0.1% $K_2HPO_4$, 0.02% $MgSO_4$ and 1% $Na_2CO_3$. A suitable agar media for enriching and identifying strains according to the invention comprises 1% skim milk, 0.025% yeast extract, 0.05% peptone, 1.5% agar and 1% $Na_2CO_3$. Both the suspending and enriching media are buffered to pH 10.5.

The enriching media is an opaque agar. Microbes that produce extracellular enzymes frequently grow the most, and are easy to see as they degrade the milk casein suspended in the agar. Consequently, a zone around the growing colony becomes clear as the opaque substance is removed, indicating the presence of protease. Colonies are plucked from the clear zones and subcultivated on to a fresh Petri plate as part of the isolation procedure.

After this preliminary characterization by enrichment and isolation, strains can be cultivated in a liquid broth. A suitable broth comprises 1% skim milk, 0.025% yeast extract, 0.05% peptone and 1% $Na_2CO_3$, buffered to pH 10.5. The proteases can be isolated from the culture broth by precipitation with ethanol, and then the activity of the proteases can be tested in detergent using various assays. Two assays which are useful are the azocasein assay and the peptidase assay.

The azocasein assay uses azocasein as the substrate and is based on the endoproteolytic activity of the enzyme. The peptidase assay uses chromogenic peptide substrate, and is based on the peptidase activity of the enzyme. Detergent interferes with both assays by reducing protease activity; however, the interference is less than 20% under the conditions used.

In the azocasein assay a solution of the enzyme is mixed with 2 ml of 0.4% azocasein in 1% $Na_2CO_3$, pH 10.5 at 38° C. At various time intervals, 0.5 ml of the reaction mixture is mixed with 0.1 ml of 60% perchloric acid. Precipitates are collected by centrifugation and the absorbance of the supernatant is measured at 440 nm. When the enzyme solution contains detergent, the maximal ratio between enzyme solution and substrate solution is set at 0.025 in order to minimize interference from the detergent.

In the peptidase assay a solution of the enzyme is mixed with 1 ml of 1% $Na_2CO_3$, pH 10.5 buffer containing 5 microliters, dissolved in ethanol, of 13 mM of N-succinyl-L-alanyl-L-alanyl-L-prolyl-L-phenylalanine-p-nitroanilide. The reaction is followed at 410 nm while the mixture is maintained at 38° C. When the enzyme solution contains detergent, the maximal ratio between enzyme solution and substrate solution is 0.02 in order to minimize interference from the detergent.

The stability of the protease in various detergents then can be assessed. Depending on the amount of activity present, protease from the fermentation broth is either used directly or is concentrated by cold precipitation with ethanol (75%). One part enzyme is mixed with three parts detergent, and the protein content averages about 1-2 grams/liter in the test.

For example, the proteases can be tested in modified Advanced Action Wisk ™. (MAAW) at 38 and 52° C. and in heavy-duty liquid Wisk ™, a detergent that does not contain enzymes, at 38° C. The proteases can also be tested in a heavy-duty detergent liquid formulation containing about 17 weight % LAS (Formula A) at various temperatures. MAAW is prepared by first denaturing the enzymes already present in Advanced Action Wisk ™ and then fortifying it with 10 grams of 50% LAS per 90 ml of detergent. The activity of the proteases is then measured with the azocasein and peptidase assays.

In searching for a bacterial strain possessing such an alkaline protease, samples were initially collected from a variety of sites. Some of the sites had neutral soils, including, for example, several samples collected from the Brazilian rain forest. Other sites had relatively alkaline or acidic soils as a result of industrial activity at the site. Sites characterized by alkaline soils included, for example, a cement plant, a tannery, and a plant that produces synthetic surfactants.

In addition to being characterized by the pH of their soils, several of the sites had soils that had been subjected to contamination by detergents, in particular by LAS or by alkylate, the raw material from which LAS is produced. This contamination was discovered to provide an additional selection pressure on the indigenous population of microorganisms in the soil, increasing the probability of finding bacteria having a protease that is stable in the presence of LAS.

Eight preferred bacterial strains which produce stable proteases according to the present invention were isolated. The eight preferred bacterial strains were isolated from 67 soil samples taken from five sites, all of which were characterized by extremely high pH and/or the presence of detergent contamination. Four of the sites were characterized by both alkaline pH and the presence of detergent contamination. In particular, three of these sites were known to have been contaminated by either alkylate or LAS. While the existence of possible detergent contamination at the fifth site could not be verified, this site was characterized by an extremely high pH of greater than 12.

Surprisingly, it was discovered that strains of bacteria having an alkaline protease characterized by excellent stability in the presence of high pH and LAS were reproducibly isolated from soils characterized by high alkalinity and/or detergent contamination. A particularly preferred strain according to the present invention was isolated from alkaline soil samples collected around several LAS storage vessels and loading docks. The strain was denoted strain 164A.

For purposes of comparison, Tables 1 and 2 below set forth the general properties of this strain and known alkalophilic Bacillus strains Y, P, K and X, each of which is disclosed in U.S. Pat. No. 4,797,362; strain 221, disclosed by K. Horikoshi, *Agr. Biol. Chem* 35(9): 1407–1414; strain 58, which is mentioned in U.S. Pat. No. 4,052,262, and strain D-6, disclosed in Japanese patent publication No. 4236 (1981).

TABLE 1

| Characteristic | Bacillus strains Y, P, K & X | 164A |
|---|---|---|
| Gram strain | + | + |
| Spores round | − | − |
| Spore location | terminal | terminal |
| Sporangium Swollen | + | + |
| Hydrolysis of | | |
| Casein | + | + |
| Starch | + | + |
| Gelatin | + | + |
| Growth at pH | | |
| 6 | + | − |
| 7 | + | + |
| 8 | + | + |
| 9 | + | + |
| 10 | + | + |
| 11 | + | + |
| 12 | + | + |
| Growth at | | |
| 20° C. | + | + |
| 37° C. | + | + |
| 47° C. | + | + |
| 52° C. | nt | + |
| Growth in Sodium | | |
| 1% | + | + |
| 5% | + | + |
| 7% | + | + |
| 10% | + | + |
| Utilization of | | |
| ammonia | − | − |
| nitrate | − | − |
| urea | + | − |
| Production of Acid from | | |
| glucose | + | + |
| sucrose | + | + |
| mannitol | + | − |
| mannose | + | + |
| fructose | + | + |
| xylose | − | − |
| lactose | − | − |
| starch | + | + |
| arabinose | − | − |
| galactose | − | − |
| maltose | + | + |

TABLE 2

| Microbiological Property | Strains Y, P, K & X | #221 | #58 | #D-6 | 164A |
|---|---|---|---|---|---|
| Utilization of Inorganic | No | Yes | Yes | Slightly | No |

TABLE 2-continued

| Microbiological Property | Strains Y, P, K & X | #221 | #58 | #D-6 | 164A |
|---|---|---|---|---|---|
| Nitrogen Sources (Ammonium salt) | | | | | |
| Growth Temperature Range | 20–47° C. | −55° C. | −45° C. | — | 20–52° C. |
| Optimal Temperature Range | 33–35° C. | 37–40° C. | 37–40° C. | 35–40° C. | — |
| Growth pH Range | 6–12 | 7–11 | 7.5–11 | 7.5–11 | 7–12 |
| Optical pH Range | around 10 | around 10 | around 10 | around 10 | |
| Saccharides as Sources for Acid Production | glucose mannose fructose maltose sucrose trehalose mannitol starch | | | In addition to those described left, arabinose xylose galactose glycerol | sucrose mannose fructose starch maltose glucose |
| Resistance to NaCl | grow in 10% NaCl | grows little in 5% NaCl | grows in 7% NaCl | grows in 5% NaCl | grows in 10% NaCl |

Like other alkalophilic Bacilli, strain 164A is gram positive and forms spores. It exhibits other properties common to the composition strains, indicating that strain 164A also is an alkalophilic Bacillus.

As the tables show, strain 164A grows well at pH 8–10 but only minimally at pH 7, and does not grow at pH 6. It grows well between 20° C. and 47° C. The strain hydrolyzes casein, starch and gelatin, and produces acids from glucose, sucrose, mannose and fructose, but not from mannitol, xylose and lactose. It has no ability to use ammonia, nitrate or urea as a sole source of nitrogen for growth. It is resistant to sodium chloride, displaying good growth in a medium containing 1–10% sodium chloride.

Strain 164A was found to produce several proteases, one of which bound to carboxymethylcellulose (CM-cellulose) at pH 7.5. This protease, which was designated protease 164A-1, was eluted from the CM-cellulose column by applying a linear gradient of 0 to 0.3M salt. It was further purified on a G75 column which separates proteins on the basis of size. Protease 164A-1 eluted in substantially pure form as the first peak out of the G75 column.

Purified protease 164A-1 was shown to have a molecular weight around 28,000 based on SDS gel electrophoresis. Protease 164A-1 was inactivated by either PMSF or DFP, an indication that it had serine in the active site. It did not lose activity in the presence of EDTA.

The total amino acid compositions of protease 164A-1 and other known Bacillus alkaline proteases are shown in Tables 3 and 4.

TABLE 3

Amino Acid Composition of Alkaline Proteases
(expressed as mols of amino acid/mol of enzyme)

| Amino Acid | Ya[1] | Yb[1] | Alcalase[2] | Subtilisin BPN'[3] | Subtilisin NOVO[4] | 164A-1 |
|---|---|---|---|---|---|---|
| Tryptophane | 5 | 11 | 1 | 3 | 3 | 2 |
| Lysine | 7 | 6 | 9 | 11 | 6 | 7 |
| Histidine | 5 | 13 | 5 | 6 | 5 | 7 |
| Arginine | 5 | 10 | 4 | 2 | 3 | 8 |
| Aspartate | 20 | 53 | 28 | 28 | 20 | 30 |
| Threonine | 11 | 18 | 19 | 13 | 14 | 17 |
| Serine | 22 | 32 | 32 | 37 | 37 | 31 |
| Glutamate | 9 | 17 | 12 | 15 | 12 | 11 |
| Proline | 9 | 14 | 9 | 14 | 10 | 9 |
| Glycine | 22 | 46 | 35 | 33 | 25 | 35 |
| Alanine | 20 | 50 | 41 | 37 | 27 | 40 |
| Valine | 9 | 35 | 31 | 30 | 20 | 30 |
| Methionine | 2 | 4 | 5 | 5 | 3 | 5 |
| Isoleucine | 6 | 15 | 10 | 13 | 12 | 13 |
| Leucine | 10 | 21 | 16 | 15 | 12 | 16 |
| Tyrosine | 6 | 14 | 13 | 10 | 9 | 11 |
| Phenylalanine | 4 | 4 | 4 | 3 | 2 | 3 |
| Cysteine | 0 | 0 | 0 | 0 | 0 | 0 |

[1]Strains Ya and Yb are disclosed in U.S. Pat. No. 4,797,362.
[2]Alcalase is disclosed in E. L. Smith, et al., J. Biol. Chem., 243:2181 (1968).
[3]Subtilisin BPN' is disclosed in F. S. Merkland, J. Biol. Chem., 242:5198 (1967).
[4]Subtilisin NOVO is disclosed in D. Turu, Agr. Biol Chem., 31:330 (1967).

TABLE 4

Amino Acid Composition of Alkaline Proteases
(expressed as mol % of residues)

| Amino Acid | Kp1239[1] | ATCC 21522[2] | 221[3] | Subtilisin carlsberg[4] | 164A-1 |
|---|---|---|---|---|---|
| Tryptophan | — | — | 1.7 | 0.36 | 0.73 |
| Lysine | 2.4 | 2.6 | 2.0 | 3.3 | 2.55 |
| Histidine | 2.4 | 2.6 | 2.8 | 1.8 | 2.55 |
| Arginine | 2.7 | 2.8 | 2.8 | 1.5 | 2.91 |
| Aspartate | 9.8 | 11.5 | 10.1 | 10.2 | 10.9 |
| Threonine | 6.8 | 6.9 | 6.3 | 6.9 | 6.18 |
| Serine | 11.7 | 11.6 | 8.0 | 11.7 | 11.27 |
| Glutamate | 6.1 | 5.8 | 5.6 | 4.4 | 4.0 |
| Proline | 5.0 | 3.6 | 5.6 | 3.3 | 3.27 |
| Glycine | 12.6 | 13.7 | 13.6 | 12.8 | 12.73 |
| Alanine | 15.2 | 16.5 | 15.6 | 15.0 | 14.55 |
| Valine | 10.5 | 10.1 | 9.4 | 11.3 | 10.9 |
| Methionine | 1.3 | 1.2 | 1.3 | 1.8 | 1.82 |
| Isoleucine | 2.8 | 2.7 | 3.1 | 3.6 | 4.73 |
| Leucine | 7.3 | 6.0 | 7.7 | 5.8 | 5.82 |
| Tyrosine | 2.8 | 2.4 | 3.1 | 4.7 | 4.00 |
| Phenylalanine | 0.68 | 0.84 | 0.7 | 1.5 | 1.09 |
| Cysteine | 0 | 0 | 0 | 0 | 0 |

[1]Kp1239 is disclosed in Y. Takii et al., Appl. Microbiol. Biotechnol., 34:57 (1990).
[2]ATCC 21522 is disclosed in Y. Suzuki, et al., Eur. J. Biochem., 158:77 (1986).
[3]Strain 221 is disclosed in K. Horikoshi, Agr. Biol. Chem., 35(9): 1407 (1971).
[4]Subtilisin carlsberg is disclosed in R. J. Delange, et al., J. Biol. Chem., 243:2134 (1968).

The complete amino acid sequence of protease 164A-1 (SEQ I1) NO; 2) is shown in FIGS. 9A and 9B, and the nucleotide sequence encoding the amino acid sequence (SEQ I1) NO: 1) is shown in FIGS. 10A–10E. The single-letter symbols for the amino acids are defines as follows:

| Amino acid | One-letter abbreviation |
| --- | --- |
| Alanine | A |
| Arginine | R |
| Asparagine | N |
| Aspartic acid | D |
| Cysteine | C |
| Glutamic acid | E |
| Glutamine | Q |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |
| Termination | * |

The mature protein, lacking a 100-residue signal peptide sequence, has a molecular weight of 28,000, based on SDS electrophoresis, and is made up of 274 amino acids with an N-terminal sequence of Ala-Gln-Thr-Thr (amino acid residues 1-4 of SEQ ID NO:2). The beginning of the mature enzyme is indicated by "▼". FIGS. 9A and 9B also presents the amino acid sequences of four other alkalophilic Bacillus: alkaline elastase ("a") (SEQ I1) NO:3), Carlsberg ("b") (SEQ I1) NO:4), B. subtilis ("c") (SEQ I1) NO:5) and B. amyloliquefaciens BPN'. The degree of homology between 164A-1 and these other strain ranged from about 60% to 75%. These percent homology with alkaline elastase was 61.1%, the percent homology with Carlsberg was 72.7%, the percent homology with B. subtilis was 67.3% and the percent homology with B. amyloliquefaciens BPN' was 69.8%. Amino acids that are conserved in all but 164A-1 are indicated with "●". Seven of the amino acids were conserved in all but protease 164A-1; these amino acids were at positions 4, 19, 50, 81, 85, 266 and 271. The boxed sequences show amino acids that are the same in 164A-1 and at least two of the other proteases.

With sequence information, like that shown in FIGS. 9A-10E, for a bacterially-evolved enzyme of the present invention, other protease-active polypeptides also can be produced which display the characteristic of high stability described above. These protease-active polypeptides are referred to here generically as "protease variants" and are exemplified by high-stability 164A-1 muteins and molecules which correspond to portions of 164A-1.

In this regard, a "164A-1 mutein" is a polypeptide that retains the basic functional attribute of protease 164A-1—namely, the stability in the presence of LAS- —and that is homologous to protease 164A-1. For purposes of this description, "homology" between two sequences connotes a likeness short of identity indicative of a derivation of the first sequence from the second. In particular, a polypeptide is "homologous" to protease 164A-1 if a comparison of amino-acid sequences between the polypeptide and 164A-1 reveals an identity of greater than about 85%. Such a sequence comparison can be performed via known algorithms, such as the one described by Lipman and Pearson, Science 227: 1435 (1985), which are readily implemented by computer.

Muteins of bacterially-evolved enzymes like protease 164A-1 can be produced, in accordance with the present invention, by conventional site-directed mutagenesis, which is one avenue for routinely identifying residues of the natural protease molecule that can be modified without rendering the resulting polypeptide biologically inactive. See CURRENT PROTOCOLS IN MOLECULAR BIOLOGY (Wiley-Interscience 1987, 1990), at Section 8 (hereafter "Ausubel et al."). Oligonucleotide-directed mutagenesis, comprising [i] synthesis of an oligonucleotide with a sequence that contains the desired nucleotide substitution (mutation), [ii] hybridizing the oligonucleotide to a template comprising a structural sequence coding for protease 164A-1 and [iii] using T4 DNA polymerase to extend the oligonucleotide as a primer, is preferred because of its ready utility in determining the effects of particular changes to the structural sequence of the bacterial enzyme. Its relative expense may militate in favor of an alternative, known direct-mutagenesis method.

Likewise within the present invention would be synthetic polypeptides that (i) correspond to a portion of the natural protease amino-acid sequence and (ii) retain an activity characteristic of the natural protease. In particular, such molecules might include a sequence in addition to a sequence that is homologous with the mature enzyme, which sequence may be cleaved.

Whether a synthetic polypeptide meeting criterion (i), such as one produced based on knowledge of the protease 164A-1 sequence shown in FIGS. 9A and 9B, also satisfies criterion (ii) can be routinely determined by means of detergent stability assays as described herein.

Variants of bacterially-evolved enzymes within the present invention could be produced by known techniques of de novo synthesis, as well as by producing a genetically-engineered host cell that expresses a protease variant encoded by a heterologous polynucleotide used to transform the host. To be used in recombinant expression of a protease 164A-1 or a 164A-1 variant, for example, a polynucleotide molecule encoding the natural or variant polypeptide preferably would comprise a nucleotide sequence, corresponding to the desired amino-acid sequence, that is optimized for the host of choice (see below) in terms of codon usage, initiation of translation, most suitable glycosylation, and expression of commercially useful amounts of protease 164A-1 or a desired variant. Also, the vector selected for transforming the chosen host organism with such a polynucleotide molecule should allow for efficient maintenance and transcription of the sequence encoding the polypeptide.

Preferred among the hosts generally available for transformation, pursuant to the present invention, are prokaryotes, as exemplified by Bacillus subtilis. For such expression systems, there are conventional transformation and screening protocols which can be employed pursuant to the present invention. See Hardy, "Bacillus Cloning Methods" in 2 DNA CLONING 1-17 (IRL Press 1985), and Lovett & Ambulos, "Genetic Manipulation of Bacillus subtilis" in BACILLUS 115-54 (Plenum Press 1989), among others. For example, transformants can be selected for expression of functional protease 164A-1 or a 164A-1 variant by use of agar plates containing skim milk, by looking for clearing of the milk plates around the colonies.

For introducing a polynucleotide of the present invention into a *B. subtilis* cell, the most commonly used protocol is transformation of competent cells with plasmid DNA (see Hardy, loc. cit.). An alternate method, protoplast transformation, can also be used.

Protease 164A-1 was found to have excellent stability at high pH and in high concentrations of anionic surfactants such as LAS. It also displayed high resistance to oxidation from bleaches, and excellent high temperature stability. This stability exceeded that of any known protease. The protease also improved detergency when blended with heavy-duty detergent liquids.

Figure 2:
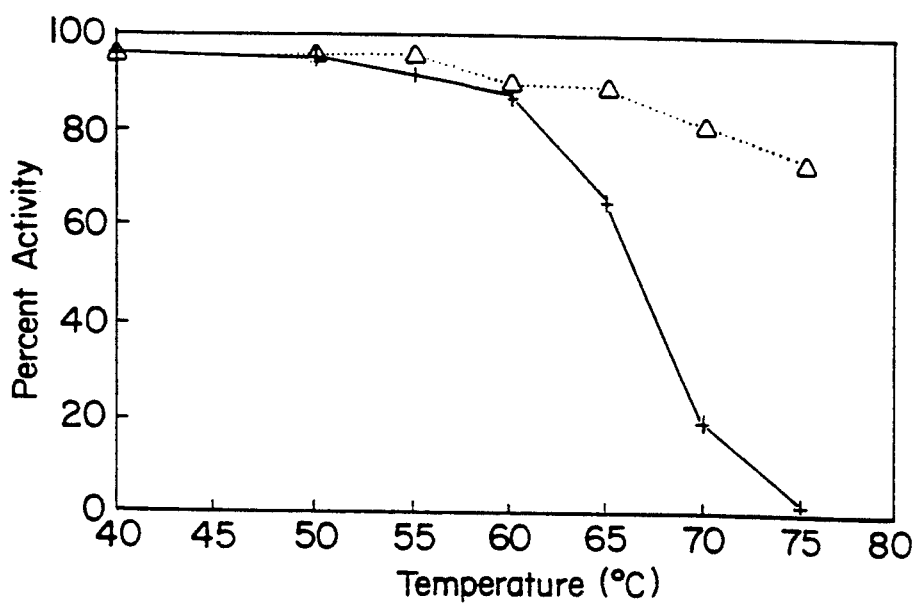
FIG. 2 shows the temperature stability of 164A-1 in the presence and absence of $Ca^{++}$.

The pH profile of protease 164A-1 is shown in FIG. 1. It is a true alkaline protease. The temperature stability of protease 164A-1 after a ten-minute incubation in the presence (Δ...Δ) and absence (x—x) of 5 mM $CaCl_2$ is presented in FIG. 2 which shows significantly improved temperature stability of protease 164A-1 in the presence of 5 mM $CaCl_2$.

The stability of the protease 164A-1 in an HDL formulation was tested in a commercial sample of Tide TM (manufactured by The Procter and Gamble Co., Cincinnati, Ohio) obtained in Chicago, Ill. This formulation had enzyme stabilizers and a pH of 8.3. The protease activity of this formulation was measured by the azocasein assay. The enzymes already contained in this formulation were first denatured by heating to 65° C. until no further enzyme activity was measurable in the sample.

A freeze-dried powder sample of the purified protease 164A-1 was then dissolved in a minimum volume of 50% propylene glycol/50% 0.2M Tris, pH 8.5 (approximately 0.05 mL) and this was then added to mL of the detergent formulation. Commercial enzyme samples from Novo Nordisk Bioindustrials were added at activity levels identical to that of the protease of this invention. The enzyme activity was chosen to provide a level of proteolytic activity equal to that of the freshest obtainable commercial HDL. The formulations were incubated at 40° C., sampled at regular intervals and assayed for protease activity.

Figure 3:
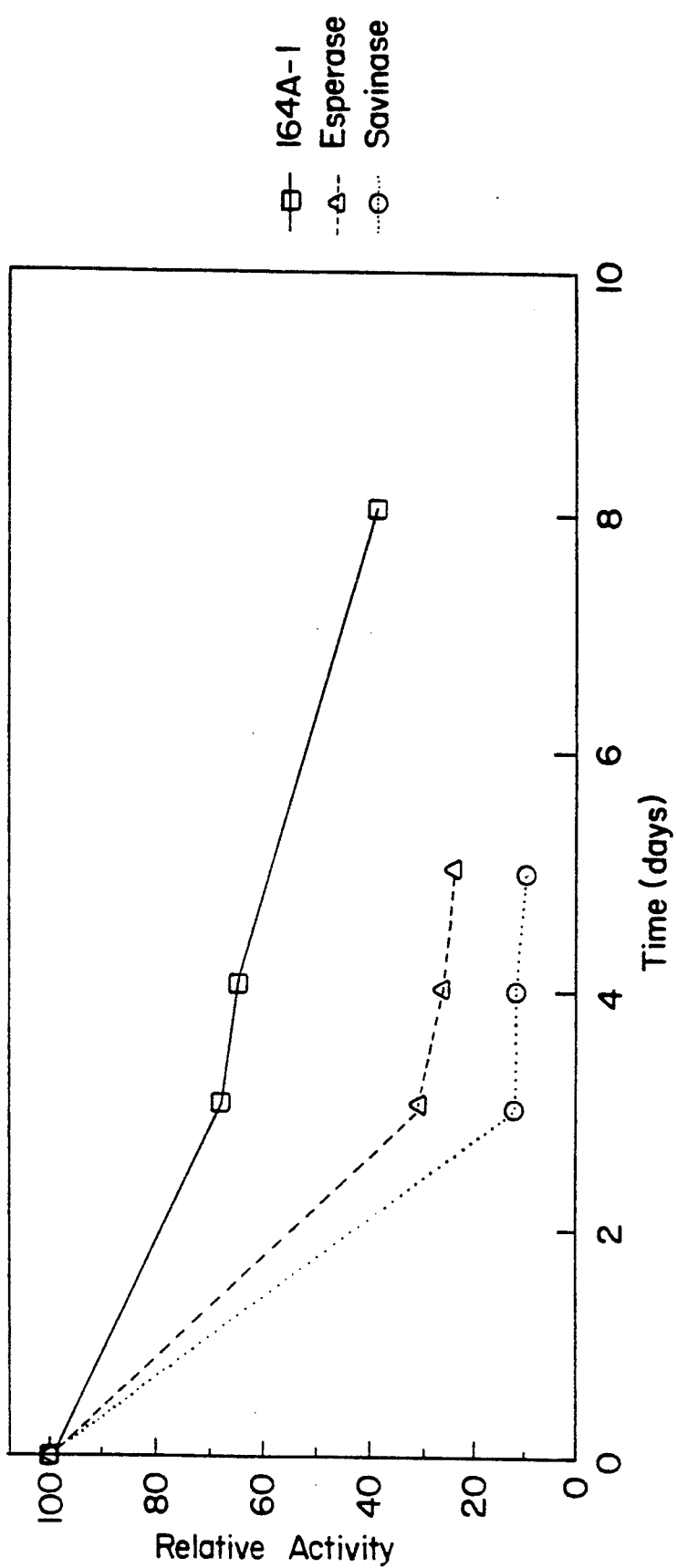
FIG. 3 compares the stability of a protease according to the present invention with that of two commercial proteases, Esperase TM and Savinase TM, in Tide TM at 40° C.

The loss of activity versus time is shown in FIG. 3. After three days, protease 164A-1 had only lost about 35% of its activity, whereas both Novo enzymes had lost at least 70% of their activity.

The stability of protease 164A-1 in other HDL formulations containing high concentrations of LAS was determined in a test similar to that conducted with liquid Tide TM. The formulations used were Advanced Action Wisk TM (manufactured by Lever Brothers Co., Edgewater, N.J.), a modification of Advanced Action Wisk TM by fortification with LAS (MAAW), Formula A and Wisk TM, a detergent liquid with no enzymes. As described above, MAAW was prepared by first denaturing any enzymes already present by heating to 65° C. for 4 hours, and then adding 50 g of SA-597 LAS (available from Vista Chemical) to 1 liter of the formulation and readjusting the pH to 9.8 with 50% NaOH, to achieve a final LAS concentration of 14 weight percent. The non-enzyme Wisk TM formulation was also modified by first lowering the pH from 10.9 to 9.8 by adding concentration HCl, and then adding 500 ppm of $CaCl_2$, before adding the enzyme.

Formula A was a stabilized aqueous detergent composition comprising:

| | |
|---|---|
| 17.2 weight % | of sodium $C_{11.5}$ alkylbenzene sulfonate (a mixture of sodium alkylbenzene sulfonates having alkyl chains of various lengths, the average number of carbon atoms in the alkyl chains being 11.5), |
| 5.2 weight % | of a condensation product of one mole of $C_{12-15}$ linear alcohol and 7 moles of ethylene oxide, |
| 5.8 weight % | of sodium sulfate ester of the condensation product of one mole $C_{12-18}$ linear alcohol and 4 moles of ethylene oxide, |
| 4.0 weight % | of sodium xylene sulfonate, |
| 5.5 weight % | of sodium citrate, |
| 1.4 weight % | of triethanolamine, |
| 1.4 weight % | of monoethanolamine, |
| 3.2 weight % | of propylene glycol, |
| 1.4 weight % | of borax, |
| 1.0 weight % | of ethanol, |
| 500 ppm | $CaCl_2$, and |
| the balance water, the pH being adjusted to 9.8. | |

The LAS contents of Formula A, Advanced Action Wisk TM, MAAW and Wisk TM were determined by the methylene blue active substances test as described in American Public Health Association, STANDARD METHODS FOR THE EXAMINATION OF WATER AND WASTEWATER (17th ed.), American Public Health Association, Washington, D.C., 1989. The results are shown in Table 5.

TABLE 5

| Formulation | Wt. % LAS | T° C. | Protease Half-Life (days) | | | |
|---|---|---|---|---|---|---|
| | | | 164A-1 | Esperase | Savinase | Alcalase |
| Advanced Action Wisk TM | 9 | 40 | >60 | >60 | 25 | 7.5 |
| Formula A | 17 | 40 | >50 | 33 | 5 | 4 |
| Formula A | 17 | 45 | 30 | 7 | ND | ND |
| LAS Fortified A.A. Wisk TM (MAAW) | 14 | 52 | 14 | 1 | 0.5 | 0.1 |
| Wisk TM | 17 | 40 | 7 | 1 | 0.75 | 1.5 |

At all temperatures in the various formulations, protease 164A-1 was significantly more stable than Esperase TM, Savinase TM and Alcalase TM, respectively.

The benefit of maintaining enzyme activity on storage in HDL was determined by measuring the detergency performance of the protease stored in the MAAW. Two inch by three inch pieces of cotton (EMPA 116) stained with blood, milk and ink were washed in a 250 mL Erlenmeyer flask at 40° C. in 75 mL of synthetic tap-water (150 ppm hardness, 3/2 Ca:Mg) and 200 μL of containing the experimental protease added activity level identical to freshly manufactured commercial HDL. At time zero, the cloth was added and the flask agitated for 30 minutes. After this treatment, the cloths were rinsed in distilled water and allowed to dry in air and the reflectances were redetermined (average of measurements). The detergency of the fresh and heat-treated Esperase ™ and protease 164A-1 samples on EMPA 116 cloth is reported in Table 6 as the change in reflectance relative to the clean cloth after the treatment (% stain remission).

TABLE 6

|  | No Enzyme | 164A-1 |  | Esperase |  |
|---|---|---|---|---|---|
|  |  | Initial | After 4 h at 65° C. | Initial | After 4 h at 65° C. |
| % Relative Activity | 0 | 100 | 68 | 100 | 0 |
| % Stain Remission | 31.1 | 63.5 | 49.8 | 65.4 | 29.8 |

The relative stability of commercial enzymes and protease 164A-1 in the presence of perborate bleach-containing powder (Tide with Bleach ™) was evaluated at typical use concentrations (1.5 g/L) at 40° C. for 15 minutes. The loss of activity in the presence of peroxide was determined by incubating the enzymes with 1 M H₂O, at 40° C. for 15 minutes as previously described by Estell et al., *J. Biol. Chem.* 243: 6518 (1985). The results are reported in Table 7.

TABLE 7

| Oxidant | % Relative Activity After Treatment | | | |
|---|---|---|---|---|
|  | 164A-1 | Esperase | Savinase | Alcalase |
| Tide with Bleach ™ | 99 | 90 | 71 | 81 |
| 1M H₂O₂ | 94 | 62 | ND | 55 |

Figure 11:
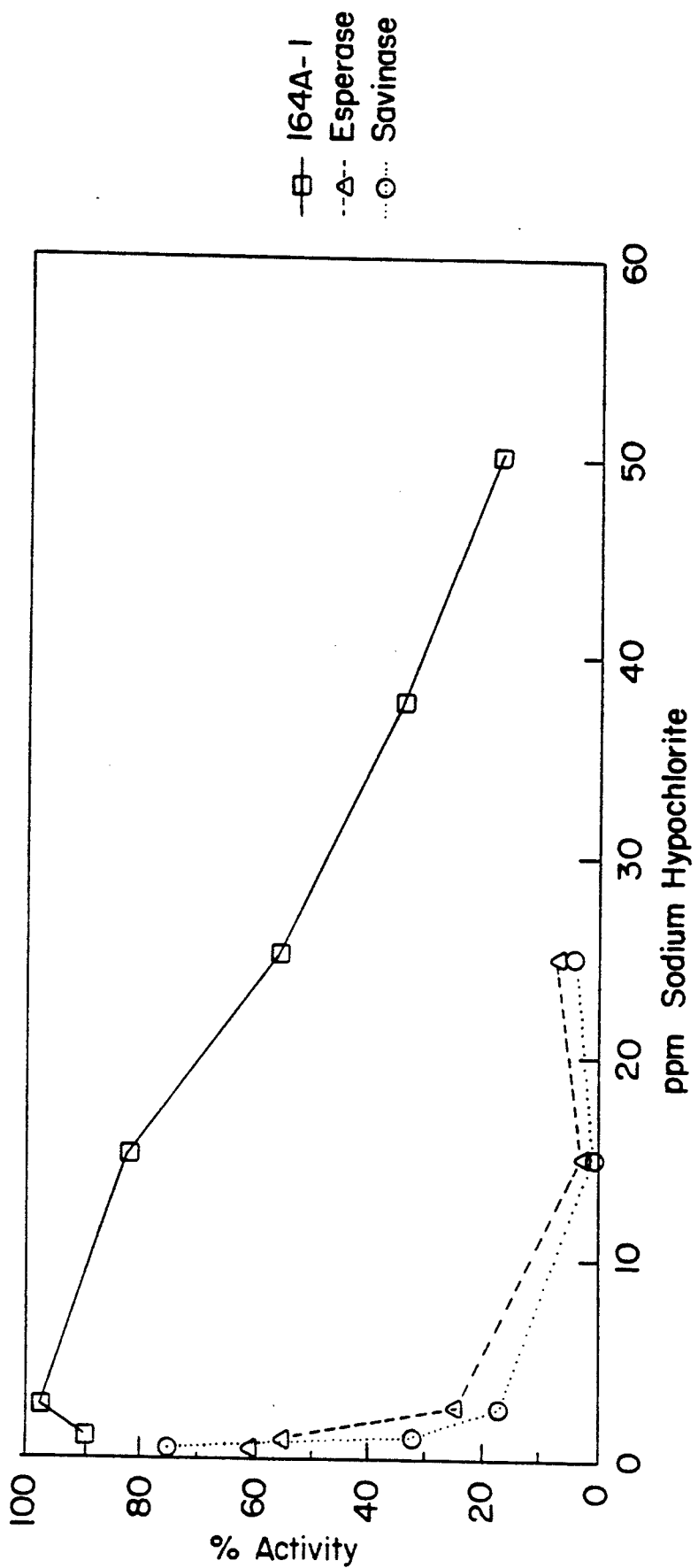
FIG. 11 shows the oxidative stability of 164A-1, Esperase TM and Savinase TM.

The effect of chlorine bleach on Esperase ™, Savinase ™ and 164A-1 was determined by treating the enzymes with various concentrations of sodium hypochlorite (Clorox ™ Bleach). Equal activities of each protease were added to 100 mL of synthetic tap-water (150 ppm hardness, Ca/Mg=3/2) containing the indicated amount of bleach. The solutions were incubated for 10 minutes at 25° C., and then a 1 mL aliquot was removed and assayed for protease activity using the azocasein assay. The results are shown in FIG. 11.

Table 8 summarizes information about protease 164A-1 and various known alkaline proteases from alkalophilic Bacillus species. Table 9 provides a comparison of the N-terminal amino acid sequences among protease 164A-1 and known Bacillus alkaline proteases.

TABLE 9

| Types of Protease | N-terminal Amino Acid Sequence |
|---|---|
| 164A-1 | Ala—Gln—Thr—Thr— (amino acid residues 1–4 of SEQ ID NO: 2) |
| Subtilisin from B. amyloliquefaciens | Ala—Gln—Ser—Val— (amino acid residues 108–111 of SEQ ID NO: 6) |
| B. subtilis | Ala—Gln—Ser—Val— (amino acid residues 107–110 of SEQ ID NO: 5) |
| B. licheniformis (Alcalase) | Ala—Gln—Thr—Val— (SEQ ID NO: 7) |
| KP1239 from B. alcalophilus | Ala—Gln—Ser—Val— (SEQ ID NO: 8) |
| Elastase YaB | Gln—Thr—Val—Pro— (amino acid residues 111–114 of SEQ ID NO: 3) |

The results reported in Tables 1, 2, 8 and 9, as well as the lipid composition of strain 164A, indicate that strain 164A belongs to genus Bacillus. Its lipid pattern does not match the lipid composition of any known Bacillus species, however. In addition, the N-terminal amino acid sequence, molecular weight, thermal stability, and total amino acid composition of 164A were quite different from that of other known alkaline proteases from alkalophilic Bacillus. It was concluded that strain 164A is a new species of Bacillus.

Figure 6:
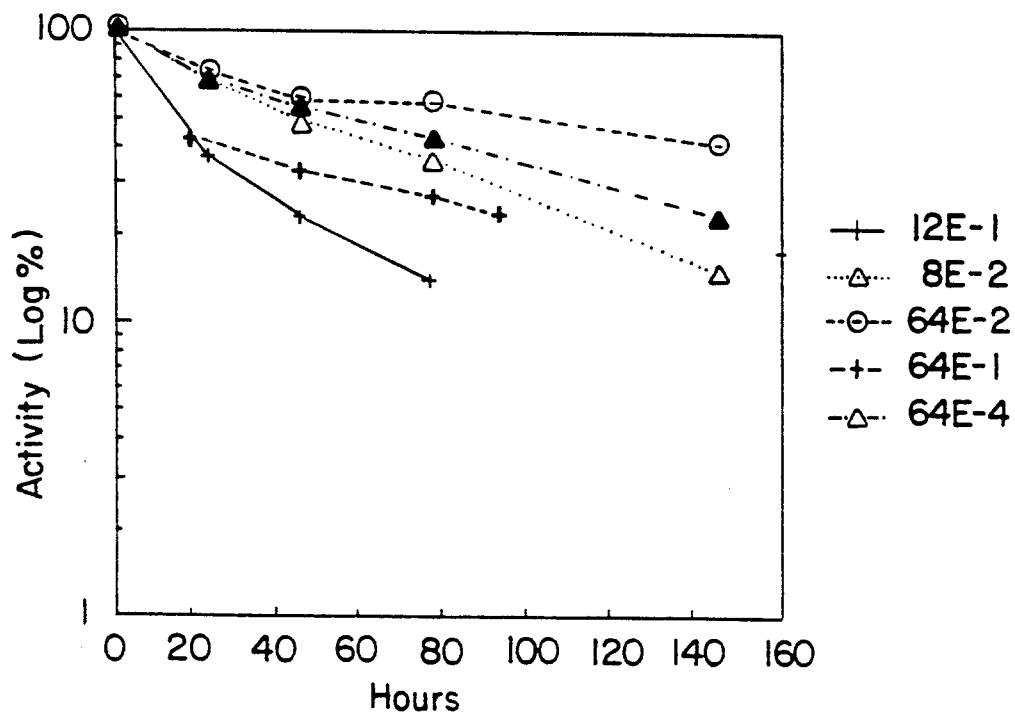
FIG. 6 shows the stability of several proteases according to the present invention in Formula A at 52° C.
Figure 7:
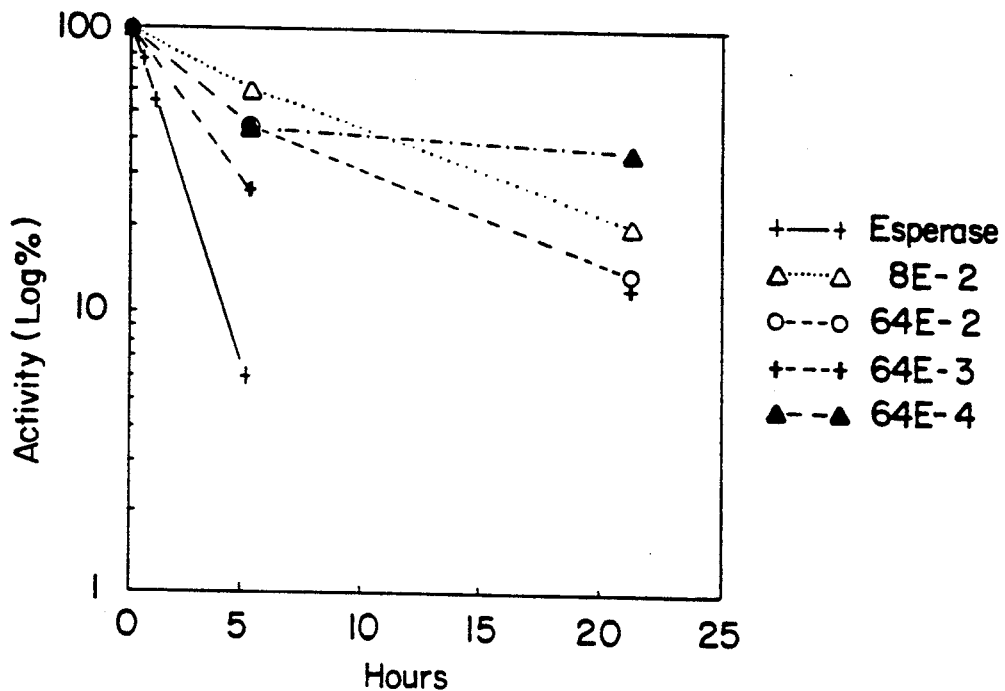
FIG. 7 shows the stability of Esperase TM and several proteases according to the present invention in Tide TM at 52° C.

While protease 164A-1 is the most preferred enzyme according to the present invention, crude proteases from the other seven isolates also displayed a much better stability in both Wisk ™ and Formula A than Esperase ™, Savinase ™, and Alcalase from Novo Nordisk Bioindustrials Inc. and Maxatase ™ and Maxacal ™ from Gist-Brocades N.V. FIG. 4A shows the stability of several proteases according to the present invention in Wisk ™ at 38° C. FIG. 4B shows the stability of Alcalase ™, Savinase ™, and Esperase ™ in Wisk ™ at 38° C. The proteases according to the invention were significantly more stable than either the Novo or Gist-Brocades enzymes. The crude proteases from isolates 8E, 12E and 64E were further purified to produce protease fractions 8E-2, 64E-1, 64E-2, 64E-3 64E-4, 12E-1, all of which showed a much better stability than commercial proteases in Formula A and Tide ™ at 52° C. See FIGS. 5, 6 and 7. In particular, as shown in FIG. 7, proteases according to the invention retain at least 25% of their activity in Ti-

TABLE 8

| Types of Protease | Optimal pH | Optimal Temp. (°C.) | Thermal Stability | | Molecular Weight | Isoelectric Point |
|---|---|---|---|---|---|---|
|  |  |  | None | 5 mM Ca++ |  |  |
| 164A-1 | 11 | 65 | 60 | 70 | 27,600 | 7.4 |
| Ya | 10–12.5 | 70 | 55 | 60 | 21,000 | 10.1 |
| Yb[1] | 9–10 | 65–70 | 50 | 60 | 40,000 | 5.1 |
| Alcalase | 10–11 | 60 | 40 | 50 | 27,300 | 9.4 |
| No. 221[2] | 11–12 | 60 | 50 | 60 | 30,000 | 9.4 |
| E-1[3] | 10–11 | 75 | 55 | 55 | 20,000 | 10.0 |
| API-21[4] | 10–11 | 45–50 | 40 |  | 22,000 | 7.4 |
| KP1239[5] | 11.5 | 60 | 55 | 54 | 29,000 | 8.8 |
| HS[6] | 9–9.5 | 70 |  |  | 36,000 | 4.2 |
| Q5[6] | 9.5 | 60 |  |  | 27,500 | 5.2 |
| Elastase YaB[7] |  |  |  |  | 26,600 | 10.6 |

Figure 8:
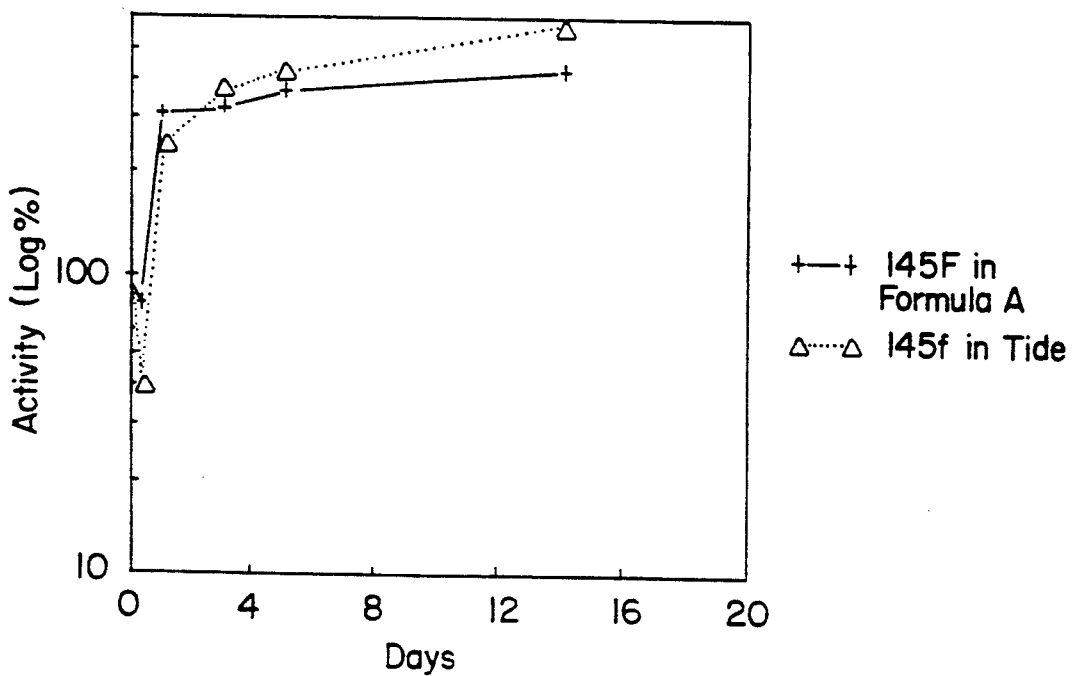
FIG. 8 shows the stability of protease 145F, a protease according to the present invention, in Formula A and Tide TM at 52° C.

[1]Strains Ya and Yb are disclosed in U.S. Pat. No. 4,797,362.
[2]Strain disclosed in K. Horikoshi, Agr. Biol. Chem. 35(9): 1407 (1971).
[3]Disclosed in Japanese patent publication No. 4236 (1981).
[4]Disclosed in Japanese patent publication No. 134990 (1983).
[5]Disclosed in Y. Takii et al., Appl. Microbiol. Biotechnol. 34: 57 (1990).
[6]Strains HS and Q5 are disclosed in U.S. Pat. No. 4,771,003.
[7]Disclosed in R. Kaneko et al., J. Bacteriol. 171: 5232 (1989).

de TM at 52° C. Another purified protease, 145F, was actually activated in both Formula A and Tide TM. In other words, the activity of this enzyme actually increased over time in the presence of Formula A and Tide TM. See FIG. 8.

Figure 5:
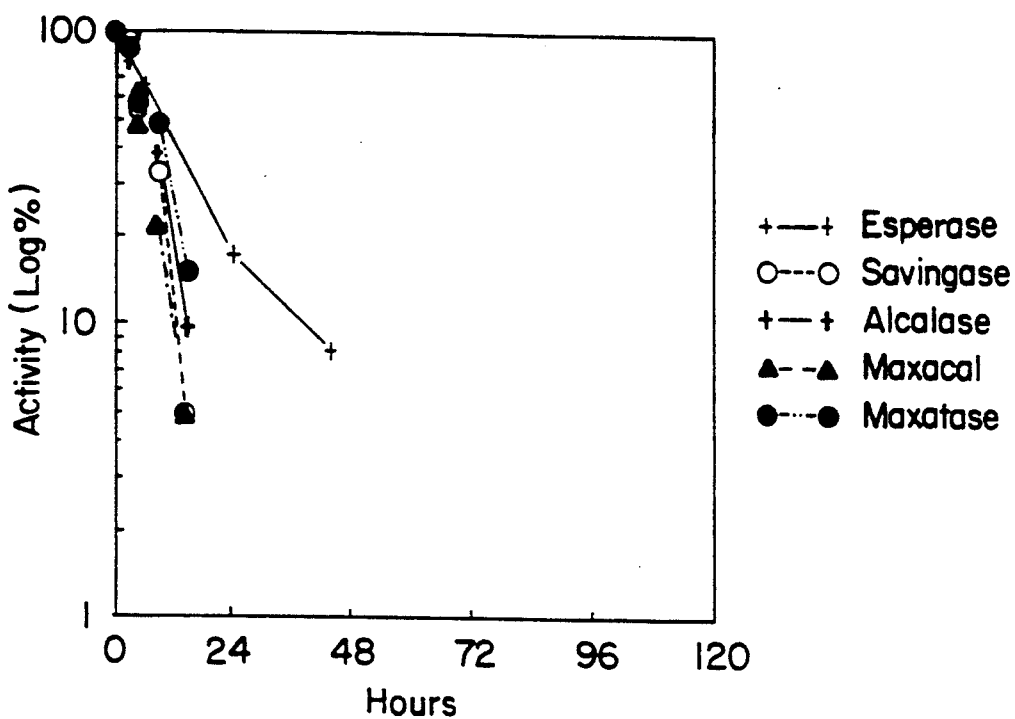
FIG. 5 shows the stability of various commercial proteases in a stabilized heavy-duty liquid detergent formulation containing 17 weight % LAS (Formula A) at 52° C.

FIG. 5 shows the stability of several proteases according to the present invention in Formula A at 52° C. All of the proteases retained at least 50% of their activity for 25 days. FIGS. 6 and 7 show the stability of Esperase TM and several proteases according to the present invention in Formula A and Tide TM at 52° C., respectively. Esperase TM lost all activity after 4 days in Formula A at 52° C. and in less than ten hours in Tide TM at 52° C. The proteases according to the present invention displayed significantly better stability than Esperase TM.

---

What is claimed is:

1. A composition containing a recoverable amount of an enzyme selected from the group consisting of purified protease enzyme 164A-1 or a purified mutein of protease enzyme 164-A1.

2. A composition as claimed in claim 1, wherein said enzyme is protease enzyme 164A-1.

3. A composition as claimed in claim 1, wherein said enzyme is a mutein of protease enzyme 164A-1.

4. A composition as claimed in claim 3, wherein said enzyme is an enzyme retaining at least 50% of its activity, according to the azocasein assay, after 12 hours at 52° C. in a stabilized aqueous solution having a pH of 9.8 and comprising 17.2 weight % of sodium $C_{11.5}$ alkylbenzene sulfonate, 5.2 weight % of a condensation product of one mole of $C_{12-15}$ linear alcohol and 7 moles of ethylene oxide, 5.8 weight % of sodium sulfate ester of the condensation product of one mole $C_{12-18}$ linear alcohol and 4 moles of ethylene oxide, 4.0 weight % of sodium xylene sulfonate, 5.5 weight % of sodium citrate, 1.4 weight % of triethanolamine, 1.4 weight % of monoethanolamine, 3.2 weight % of propylene glycol, 1.4 weight % of borax, 1.0 weight % of alcohol, 500 ppm $CaCl_2$, and the balance water.

5. A composition according to claim 4, wherein said enzyme retains at least 50% of its activity after 12 days.

6. An isolated polynucleotide molecule that encodes protease enzyme 164A-1 or a mutein of protease enzyme 164A-1.

7. An isolated polynucleotide molecule according to claim 6 that encodes protease enzyme 164A-1.

8. An isolated polynucleotide molecule according to claim 6 that encodes a mutein of protease enzyme 164A-1.

9. An isolated polynucleotide molecule as claimed in claim 8, wherein the enzyme encoded by the polynucleotide molecule is an enzyme that retains at least 50% of its activity, according to the azocasein assay, after 12 hours at 52° C. in a stabilized solution having a pH of 9.8 and comprising 17.2 weight % of sodium $C_{11.5}$ alkylbenzene sulfonate, 5.2 weight % of a condensation product of one mole of $C_{12-15}$ linear alcohol and 7 moles of ethylene oxide, 5.8 weight % of sodium sulfate ester of the condensation product of one mole $C_{12-18}$ linear alcohol and 4 moles of ethylene oxide, 4.0 weight % of sodium xylene sulfonate, 5.5 weight % of sodium citrate, 1.4 weight % of triethanolamine, 1.4 weight % of monoethanolamine, 3.2 weight % of propylene glycol, 1.4 weight % of borax, 1.0 weight % of ethanol, 500 ppm $CaCl_2$, and the balance water.

10. An isolated polynucleotide molecule as claimed in claim 9, wherein the enzyme encoded by the polynucleotide molecule is an enzyme that retains at least 50% of its activity after 12 days.

11. A genetically-engineered host cell that expresses an enzyme encoded by a heterologous polynucleotide as recited in claim 6.

12. A genetically-engineered host cell that expresses an enzyme encoded by a heterologous polynucleotide as recited in claim 7.

13. A genetically-engineered host cell that expresses an enzyme encoded by a heterologous polynucleotide as recited in claim 8.

14. A genetically-engineered host cell that expresses an enzyme encoded by a heterologous polynucleotide as recited in claim 9.

15. A genetically-engineered host cell that expresses an enzyme encoded by a heterologous polynucleotide as recited in claim 10.

* * * * *